United States Patent
Zdeblick et al.

(10) Patent No.: US 9,014,779 B2
(45) Date of Patent: Apr. 21, 2015

(54) DATA GATHERING SYSTEM

(75) Inventors: Mark Zdeblick, Portola Valley, CA (US); James Hutchison, Palo Alto, CA (US); Lawrence Arne, Palo Alo, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 0 days.

(21) Appl. No.: 13/377,339

(22) PCT Filed: Jan. 28, 2011

(86) PCT No.: PCT/US2011/023013
§ 371 (c)(1),
(2), (4) Date: Dec. 9, 2011

(87) PCT Pub. No.: WO2011/094606
PCT Pub. Date: Aug. 4, 2011

(65) Prior Publication Data
US 2012/0116201 A1 May 10, 2012

Related U.S. Application Data

(60) Provisional application No. 61/300,435, filed on Feb. 1, 2010, provisional application No. 61/378,878, filed on Aug. 31, 2010.

(51) Int. Cl.
*A61B 5/04* (2006.01)
*A61B 5/0408* (2006.01)
(Continued)

(52) U.S. Cl.
CPC ............ *A61B 5/0408* (2013.01); *H04B 13/005* (2013.01); *A61B 5/061* (2013.01);
(Continued)

(58) Field of Classification Search
USPC ............................ 600/372, 382, 393; 439/909
See application file for complete search history.

(56) References Cited

U.S. PATENT DOCUMENTS 3,607,788 A 9/1971 Adolph
3,642,008 A 2/1972 Bolduc
(Continued)

FOREIGN PATENT DOCUMENTS

CN 1991868 7/2007
CN 101005470 7/2007
(Continued)

OTHER PUBLICATIONS

Prutchi et al "Design and Development of Medical Electronic Instrumentation: A Practical Perspective of the Design, Construction, and Test of Medical Devices," Wiley-Interscience (2005) pp. 12-14.*
(Continued)

*Primary Examiner* — Lee S Cohen
*Assistant Examiner* — Erin M Cardinal
(74) *Attorney, Agent, or Firm* — K&L Gates LLP (57) ABSTRACT

A device for gathering data has first and second electrodes. The first electrode is coupled to a surface of interest, and the second electrode is coupled to "everything else" or "the air". The first electrode is shielded from the second, and from most sources of parasitic capacitance, by a shield that is driven by an active driver that drives the shield to track, and ideally to match, the instantaneous potential of the electrode. The second electrode is likewise shielded in a similar way from most sources of parasitic capacitance. These shields likewise help to limit the extent to which RFI from the device electronics couples with either of the electrodes. In this way the sensing device achieves a markedly better signal-to-noise ratio at frequency bands of interest.

15 Claims, 1 Drawing Sheet

(51) Int. Cl.
*H04B 13/00* (2006.01)
*A61B 5/06* (2006.01)
*A61B 5/00* (2006.01)
*A61J 7/04* (2006.01)
*G06F 19/00* (2011.01)
*A61K 9/20* (2006.01)
*A61B 5/07* (2006.01)

(52) U.S. Cl.
CPC ............ *A61B 5/681* (2013.01); *A61J 7/0481* (2013.01); *G06F 19/3456* (2013.01); *A61K 9/20* (2013.01); *A61B 5/07* (2013.01); *A61J 2007/0418* (2013.01); *A61J 2007/049* (2013.01); *A61J 2200/30* (2013.01); *A61J 2205/60* (2013.01)

(56) References Cited

U.S. PATENT DOCUMENTS

| | | |
|---|---|---|
| 3,679,480 A | 7/1972 | Brown et al. |
| 3,682,160 A | 8/1972 | Murata |
| 3,719,183 A | 3/1973 | Schwartz |
| 3,812,854 A | 5/1974 | Michaels et al. |
| 3,828,766 A | 8/1974 | Krasnow |
| 3,837,339 A | 9/1974 | Aisenberg et al. |
| 3,880,146 A * | 4/1975 | Everett et al. ............... 600/523 |
| 3,989,050 A | 11/1976 | Buchalter |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,121,573 A | 10/1978 | Crovella et al. |
| 4,129,125 A | 12/1978 | Lester |
| 4,166,453 A | 9/1979 | McClelland |
| 4,239,046 A | 12/1980 | Ong |
| 4,269,189 A | 5/1981 | Abraham |
| 4,331,654 A | 5/1982 | Morris |
| 4,345,588 A | 8/1982 | Widder et al. |
| 4,403,989 A | 9/1983 | Christensen et al. |
| 4,418,697 A | 12/1983 | Tama |
| 4,425,117 A | 1/1984 | Hugemann |
| 4,475,905 A | 10/1984 | Himmelstrup |
| 4,487,602 A | 12/1984 | Christensen et al. |
| 4,494,950 A | 1/1985 | Fischell |
| 4,529,401 A | 7/1985 | Leslie et al. |
| 4,551,133 A | 11/1985 | Zegers de Beyl et al. |
| 4,559,950 A | 12/1985 | Vaughan |
| 4,578,061 A | 3/1986 | Lemelson |
| 4,621,644 A * | 11/1986 | Eilers ........................ 600/405 |
| 4,635,641 A | 1/1987 | Hoffman |
| 4,654,165 A | 3/1987 | Eisenber |
| 4,669,479 A * | 6/1987 | Dunseath, Jr. ............... 600/391 |
| 4,705,503 A | 11/1987 | Dorman et al. |
| 4,725,997 A | 2/1988 | Urquhart et al. |
| 4,763,659 A | 8/1988 | Dunseath |
| 4,784,162 A | 11/1988 | Ricks |
| 4,793,825 A | 12/1988 | Benjamin et al. |
| 4,795,429 A | 1/1989 | Feldstein |
| 4,809,705 A | 3/1989 | Ascher |
| 4,844,076 A | 7/1989 | Lesho et al. |
| 4,850,967 A | 7/1989 | Cosmai |
| 4,858,617 A | 8/1989 | Sanders |
| 4,896,261 A | 1/1990 | Nolan |
| 4,911,916 A | 3/1990 | Cleary |
| 4,922,901 A | 5/1990 | Brooks et al. |
| 4,975,230 A | 12/1990 | Pinkhasov |
| 4,987,897 A | 1/1991 | Funke |
| 5,006,342 A | 4/1991 | Cleary et al. |
| 5,016,634 A | 5/1991 | Vock et al. |
| 5,079,006 A | 1/1992 | Urguhart |
| 5,125,888 A | 6/1992 | Howard et al. |
| 5,135,479 A | 8/1992 | Sibalis et al. |
| 5,156,911 A | 10/1992 | Stewart |
| 5,167,626 A | 12/1992 | Casper |
| 5,167,649 A | 12/1992 | Zook |
| 5,176,626 A | 1/1993 | Soehendra |
| 5,190,522 A | 3/1993 | Wojcicki et al. |
| 5,205,292 A | 4/1993 | Czar et al. |
| 5,213,568 A | 5/1993 | Lattin et al. |
| 5,245,332 A | 9/1993 | Katzenstein et al. |
| 5,246,418 A | 9/1993 | Haynes et al. |
| 5,261,402 A | 11/1993 | DiSabito |
| 5,263,481 A | 11/1993 | Axelgaard et al. |
| 5,281,287 A | 1/1994 | Lloyd |
| 5,283,136 A | 2/1994 | Peled et al. |
| 5,284,133 A | 2/1994 | Burns et al. |
| 5,300,299 A | 4/1994 | Sweet et al. |
| 5,317,506 A | 5/1994 | Coutre et al. |
| 5,318,557 A | 6/1994 | Gross |
| 5,331,953 A | 7/1994 | Andersson et al. |
| 5,351,695 A | 10/1994 | Mills et al. |
| 5,363,842 A | 11/1994 | Mishelevich et al. |
| 5,364,838 A | 11/1994 | Rubsamen |
| 5,394,866 A | 3/1995 | Ritson et al. |
| 5,394,882 A | 3/1995 | Mawhinney |
| 5,404,871 A | 4/1995 | Goodman et al. |
| 5,415,866 A | 5/1995 | Zook |
| 5,423,750 A | 6/1995 | Spiller |
| 5,458,141 A | 10/1995 | Neil et al. |
| 5,479,920 A | 1/1996 | Piper et al. |
| 5,485,841 A | 1/1996 | Watkin et al. |
| 5,487,378 A | 1/1996 | Robertson et al. |
| 5,505,195 A | 4/1996 | Wolf et al. |
| 5,505,958 A | 4/1996 | Bello et al. |
| 5,507,277 A | 4/1996 | Rubsamen et al. |
| 5,509,404 A | 4/1996 | Lloyd et al. |
| 5,511,548 A | 4/1996 | Riazzi et al. |
| 5,522,378 A | 6/1996 | Ritson et al. |
| 5,527,288 A | 6/1996 | Gross et al. |
| 5,536,503 A | 7/1996 | Kitchell et al. |
| 5,540,669 A | 7/1996 | Sage et al. |
| 5,542,410 A | 8/1996 | Goodman et al. |
| 5,556,421 A | 9/1996 | Prutchi et al. |
| 5,570,682 A | 11/1996 | Johnson |
| 5,586,550 A | 12/1996 | Ivri et al. |
| 5,587,237 A | 12/1996 | Korpman |
| 5,593,390 A | 1/1997 | Castellano et al. |
| 5,596,302 A | 1/1997 | Mastrocola et al. |
| D377,983 S | 2/1997 | Sabri et al. |
| RE35,474 E | 3/1997 | Woodard et al. |
| 5,608,647 A | 3/1997 | Rubsamen et al. |
| 5,616,124 A | 4/1997 | Hague et al. |
| 5,622,162 A | 4/1997 | Johansson et al. |
| 5,622,180 A | 4/1997 | Tammi et al. |
| 5,634,466 A | 6/1997 | Gruner |
| 5,634,468 A | 6/1997 | Platt |
| 5,634,899 A | 6/1997 | Shapland et al. |
| 5,645,063 A | 7/1997 | Straka et al. |
| 5,645,855 A | 7/1997 | Lorenz |
| 5,655,516 A | 8/1997 | Goodman et al. |
| 5,655,523 A | 8/1997 | Hodson et al. |
| 5,656,286 A | 8/1997 | Miranda et al. |
| 5,666,945 A | 9/1997 | Davenport |
| 5,676,129 A | 10/1997 | Rocci, Jr. et al. |
| 5,686,099 A | 11/1997 | Sablotsky et al. |
| 5,688,232 A | 11/1997 | Flower |
| 5,694,919 A | 12/1997 | Rubsamen et al. |
| 5,694,920 A | 12/1997 | Abrams et al. |
| 5,697,899 A | 12/1997 | Hillman et al. |
| 5,709,202 A | 1/1998 | Lloyd et al. |
| 5,713,349 A | 2/1998 | Keaney |
| 5,720,771 A | 2/1998 | Snell |
| 5,724,986 A | 3/1998 | Jones, Jr. et al. |
| 5,740,793 A | 4/1998 | Hodson et al. |
| 5,740,811 A | 4/1998 | Hedberg |
| 5,746,711 A | 5/1998 | Sibalis et al. |
| 5,781,442 A | 7/1998 | Engleson et al. |
| 5,792,048 A | 8/1998 | Schaefer |
| 5,794,612 A | 8/1998 | Wachter et al. |
| 5,802,467 A | 9/1998 | Salazar |
| 5,807,375 A | 9/1998 | Gross et al. |
| 5,809,997 A | 9/1998 | Wolf |

(56) References Cited

U.S. PATENT DOCUMENTS

| | | | |
|---|---|---|---|
| 5,810,888 A | 9/1998 | Fenn | |
| 5,813,397 A | 9/1998 | Goodman et al. | |
| 5,823,179 A | 10/1998 | Grychowski et al. | |
| 5,826,570 A | 10/1998 | Goodman et al. | |
| 5,830,175 A | 11/1998 | Flower | |
| 5,833,716 A | 11/1998 | Bar-Or | |
| 5,839,430 A | 11/1998 | Cama | |
| 5,843,014 A | 12/1998 | Lattin et al. | |
| 5,845,265 A | 12/1998 | Woolston | |
| 5,848,991 A | 12/1998 | Gross et al. | |
| 5,851,197 A | 12/1998 | Marano et al. | |
| 5,857,994 A | 1/1999 | Flower | |
| 5,860,957 A | 1/1999 | Jacobsen et al. | |
| 5,862,803 A | 1/1999 | Besson | |
| 5,862,808 A | 1/1999 | Albarello | |
| 5,865,786 A | 2/1999 | Sibalis et al. | |
| 5,865,787 A | 2/1999 | Shapland et al. | |
| 5,868,136 A | 2/1999 | Fox | |
| 5,873,835 A | 2/1999 | Hastings et al. | |
| 5,894,841 A | 4/1999 | Voges | |
| 5,906,579 A | 5/1999 | Vander et al. | |
| 5,906,597 A | 5/1999 | McPhee et al. | |
| 5,921,237 A | 7/1999 | Eisele et al. | |
| 5,921,925 A | 7/1999 | Cartmell et al. | |
| 5,924,997 A | 7/1999 | Campbell | |
| 5,925,021 A | 7/1999 | Castellano et al. | |
| 5,925,030 A | 7/1999 | Gross et al. | |
| 5,925,066 A | 7/1999 | Kroll et al. | |
| 5,928,201 A | 7/1999 | Poulsen et al. | |
| 5,957,854 A | 9/1999 | Besson et al. | |
| 5,960,792 A | 10/1999 | Lloyd et al. | |
| 5,967,986 A | 10/1999 | Cimochowski et al. | |
| 5,967,989 A | 10/1999 | Cimochowski et al. | |
| 5,974,124 A | 10/1999 | Schlueter, Jr. et al. | |
| 5,981,166 A | 11/1999 | Mandecki | |
| 5,991,655 A | 11/1999 | Gross et al. | |
| 5,997,501 A | 12/1999 | Gross et al. | |
| 5,999,846 A | 12/1999 | Pardey et al. | |
| 6,006,747 A | 12/1999 | Eisele et al. | |
| 6,012,454 A | 1/2000 | Hodson et al. | |
| 6,018,680 A | 1/2000 | Flower | |
| 6,023,631 A | 2/2000 | Cartmell et al. | |
| 6,024,976 A | 2/2000 | Miranda et al. | |
| 6,029,083 A | 2/2000 | Flower et al. | |
| 6,038,464 A | 3/2000 | Axelgaard et al. | |
| 6,042,710 A | 3/2000 | Dubrow | |
| 6,047,203 A | 4/2000 | Sackner | |
| 6,053,873 A | 4/2000 | Govari et al. | |
| 6,053,888 A | 4/2000 | Kong | |
| 6,055,980 A | 5/2000 | Mecikalski et al. | |
| RE36,754 E | 6/2000 | Noel | |
| 6,076,016 A | 6/2000 | Feierbach | |
| 6,076,519 A | 6/2000 | Johnson | |
| 6,081,734 A | 6/2000 | Batz | |
| 6,085,740 A | 7/2000 | Ivri et al. | |
| 6,085,742 A | 7/2000 | Wachter | |
| 6,095,141 A | 8/2000 | Armer et al. | |
| 6,095,985 A | 8/2000 | Raymond et al. | |
| 6,105,571 A | 8/2000 | Coffee | |
| 6,109,260 A | 8/2000 | Bathe | |
| 6,116,233 A | 9/2000 | Denyer et al. | |
| 6,117,077 A | 9/2000 | Del Mar et al. | |
| 6,119,684 A | 9/2000 | Nohl et al. | |
| 6,122,351 A | 9/2000 | Schlueter, Jr. et al. | |
| 6,125,844 A | 10/2000 | Samiotes | |
| 6,141,592 A | 10/2000 | Pauly | |
| 6,142,146 A | 11/2000 | Abrams et al. | |
| 6,148,815 A | 11/2000 | Wolf | |
| 6,152,130 A | 11/2000 | Abrams et al. | |
| 6,196,218 B1 | 3/2001 | Voges | |
| 6,196,219 B1 | 3/2001 | Hess et al. | |
| 6,198,966 B1 | 3/2001 | Heruth | |
| 6,200,265 B1 | 3/2001 | Walsh et al. | |
| 6,200,625 B1 | 3/2001 | Beckett | |
| 6,202,642 B1 | 3/2001 | McKinnon et al. | |
| 6,204,764 B1 | 3/2001 | Maloney | |
| 6,206,702 B1 | 3/2001 | Hayden et al. | |
| 6,217,744 B1 | 4/2001 | Crosby | |
| 6,221,383 B1 | 4/2001 | Miranda et al. | |
| 6,231,560 B1 | 5/2001 | Bui et al. | |
| 6,231,593 B1 | 5/2001 | Meserol | |
| 6,237,398 B1 | 5/2001 | Porat et al. | |
| 6,237,589 B1 | 5/2001 | Denyer et al. | |
| 6,237,594 B1 | 5/2001 | Davenport | |
| 6,238,338 B1 | 5/2001 | DeLuca et al. | |
| 6,245,026 B1 | 6/2001 | Campbell et al. | |
| 6,245,057 B1 | 6/2001 | Sieben et al. | |
| 6,251,079 B1 | 6/2001 | Gambale et al. | |
| 6,254,573 B1 | 7/2001 | Haim et al. | |
| 6,256,533 B1 | 7/2001 | Yuzhakov et al. | |
| 6,260,549 B1 | 7/2001 | Sosiak | |
| 6,269,340 B1 | 7/2001 | Ford et al. | |
| 6,272,370 B1 | 8/2001 | Gillies et al. | |
| 6,275,476 B1 | 8/2001 | Wood | |
| 6,283,951 B1 | 9/2001 | Flaherty et al. | |
| 6,283,953 B1 | 9/2001 | Ayer et al. | |
| 6,285,897 B1 | 9/2001 | Kilcoyne et al. | |
| 6,287,252 B1 | 9/2001 | Lugo | |
| 6,289,238 B1 | 9/2001 | Besson et al. | |
| 6,309,370 B1 | 10/2001 | Haim et al. | |
| 6,315,719 B1 | 11/2001 | Rode et al. | |
| 6,316,022 B1 | 11/2001 | Mantelle | |
| 6,318,361 B1 | 11/2001 | Sosiak | |
| 6,327,486 B1 * | 12/2001 | Nissila et al. | 600/372 |
| 6,340,357 B1 | 1/2002 | Poulsen et al. | |
| 6,349,724 B1 | 2/2002 | Burton et al. | |
| 6,352,715 B1 | 3/2002 | Hwang et al. | |
| 6,358,202 B1 | 3/2002 | Arent | |
| 6,364,834 B1 | 4/2002 | Reuss | |
| 6,366,206 B1 | 4/2002 | Ishikawa et al. | |
| 6,371,927 B1 | 4/2002 | Brune | |
| 6,374,670 B1 | 4/2002 | Spelman | |
| 6,377,848 B1 | 4/2002 | Garde et al. | |
| 6,378,520 B1 | 4/2002 | Davenport | |
| 6,380,858 B1 | 4/2002 | Yarin et al. | |
| 6,385,488 B1 | 5/2002 | Flower et al. | |
| 6,390,088 B1 | 5/2002 | Nohl et al. | |
| 6,394,953 B1 | 5/2002 | Devlin et al. | |
| 6,394,997 B1 | 5/2002 | Lemelson | |
| 6,397,838 B1 | 6/2002 | Zimlich et al. | |
| 6,406,426 B1 | 6/2002 | Reuss et al. | |
| 6,413,238 B1 | 7/2002 | Maget | |
| 6,422,236 B1 | 7/2002 | Nilsson | |
| 6,425,392 B1 | 7/2002 | Sosiak | |
| 6,426,863 B1 | 7/2002 | Munshi | |
| 6,427,684 B2 | 8/2002 | Ritsche et al. | |
| 6,431,171 B1 | 8/2002 | Burton | |
| 6,432,292 B1 | 8/2002 | Pinto et al. | |
| 6,435,175 B1 | 8/2002 | Stenzler | |
| 6,440,069 B1 | 8/2002 | Raymond et al. | |
| 6,441,747 B1 | 8/2002 | Khair | |
| 6,443,146 B1 | 9/2002 | Voges | |
| 6,448,303 B1 | 9/2002 | Paul | |
| 6,453,195 B1 | 9/2002 | Thompson | |
| 6,468,242 B1 | 10/2002 | Wilson et al. | |
| 6,477,424 B1 | 11/2002 | Thompson et al. | |
| 6,482,156 B2 | 11/2002 | Lliff | |
| 6,484,721 B1 | 11/2002 | Bliss | |
| 6,485,461 B1 | 11/2002 | Mason et al. | |
| 6,494,829 B1 | 12/2002 | New et al. | |
| 6,496,705 B1 | 12/2002 | Ng et al. | |
| 6,516,796 B1 | 2/2003 | Cox et al. | |
| 6,517,481 B2 | 2/2003 | Hoek et al. | |
| 6,517,527 B2 | 2/2003 | Gambale et al. | |
| 6,520,928 B1 | 2/2003 | Junior et al. | |
| 6,526,315 B1 | 2/2003 | Inagawa | |
| 6,527,759 B1 | 3/2003 | Tachibana et al. | |
| 6,533,733 B1 | 3/2003 | Ericson et al. | |
| 6,536,423 B2 | 3/2003 | Conway | |
| 6,540,154 B1 | 4/2003 | Ivri et al. | |
| 6,544,174 B2 | 4/2003 | West | |
| 6,564,079 B1 | 5/2003 | Cory | |
| 6,564,093 B1 | 5/2003 | Ostrow et al. | |
| 6,568,390 B2 | 5/2003 | Nichols et al. | |

(56) References Cited

U.S. PATENT DOCUMENTS

| | | |
|---|---|---|
| 6,575,932 B1 | 6/2003 | O'Brien et al. |
| 6,577,893 B1 | 6/2003 | Besson et al. |
| 6,578,741 B2 | 6/2003 | Ritsche et al. |
| 6,579,231 B1 | 6/2003 | Phipps |
| 6,582,393 B2 | 6/2003 | Sage |
| 6,584,971 B1 | 7/2003 | Denyer et al. |
| 6,585,698 B1 | 7/2003 | Packman et al. |
| 6,589,229 B1 | 7/2003 | Connelly et al. |
| 6,599,281 B1 | 7/2003 | Struys et al. |
| 6,605,038 B1 | 8/2003 | Teller et al. |
| 6,605,046 B1 | 8/2003 | Del Mar |
| 6,605,072 B2 | 8/2003 | Struys et al. |
| 6,606,989 B1 | 8/2003 | Brand et al. |
| 6,607,508 B2 | 8/2003 | Knauer |
| 6,609,018 B2 | 8/2003 | Cory |
| 6,612,984 B1 | 9/2003 | Kerr |
| 6,615,827 B2 | 9/2003 | Greenwood et al. |
| 6,629,524 B1 | 10/2003 | Goodall et al. |
| 6,632,175 B1 | 10/2003 | Marshall |
| 6,632,216 B2 | 10/2003 | Houzego et al. |
| 6,640,804 B2 | 11/2003 | Ivri et al. |
| 6,643,541 B2 | 11/2003 | Mok et al. |
| 6,651,651 B1 | 11/2003 | Bonney et al. |
| 6,654,638 B1 | 11/2003 | Sweeney |
| 6,655,381 B2 | 12/2003 | Keane et al. |
| 6,656,148 B2 | 12/2003 | Das et al. |
| 6,663,846 B1 | 12/2003 | McCombs |
| 6,673,474 B2 | 1/2004 | Yamamoto |
| 6,678,555 B2 | 1/2004 | Flower et al. |
| 6,680,923 B1 | 1/2004 | Leon |
| 6,685,648 B2 | 2/2004 | Flaherty et al. |
| 6,689,117 B2 | 2/2004 | Sweeney et al. |
| 6,694,161 B2 | 2/2004 | Mehrotra |
| 6,704,602 B2 | 3/2004 | Berg et al. |
| 6,705,316 B2 | 3/2004 | Blythe et al. |
| 6,715,487 B2 | 4/2004 | Nichols et al. |
| 6,720,923 B1 | 4/2004 | Hayward et al. |
| 6,723,077 B2 | 4/2004 | Pickup et al. |
| 6,726,661 B2 | 4/2004 | Munk et al. |
| 6,728,574 B2 | 4/2004 | Ujhelyi et al. |
| 6,738,671 B2 | 5/2004 | Christphersom et al. |
| 6,740,033 B1 | 5/2004 | Olejniczak et al. |
| 6,745,082 B2 | 6/2004 | Axelgaard et al. |
| 6,745,761 B2 | 6/2004 | Christrup et al. |
| 6,745,764 B2 | 6/2004 | Hickle |
| 6,746,429 B2 | 6/2004 | Sadowski et al. |
| 6,748,945 B2 | 6/2004 | Grychowski et al. |
| 6,755,783 B2 | 6/2004 | Cosentino |
| 6,757,523 B2 | 6/2004 | Fry |
| 6,796,305 B1 | 9/2004 | Banner et al. |
| 6,796,956 B2 | 9/2004 | Hartlaub et al. |
| 6,800,060 B2 | 10/2004 | Marshall |
| 6,801,137 B2 | 10/2004 | Eggers et al. |
| 6,807,965 B1 | 10/2004 | Hickle |
| 6,810,290 B2 | 10/2004 | Lebel et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,854,461 B2 | 2/2005 | Nichols et al. |
| 6,856,832 B1 | 2/2005 | Matsumura et al. |
| 6,858,011 B2 | 2/2005 | Sehgal |
| 6,864,780 B2 | 3/2005 | Doi |
| 6,866,037 B1 | 3/2005 | Aslin et al. |
| 6,879,810 B2 | 4/2005 | Bouet |
| 6,882,881 B1 | 4/2005 | Lesser et al. |
| 6,886,557 B2 | 5/2005 | Childers et al. |
| 6,893,415 B2 | 5/2005 | Madsen et al. |
| 6,897,788 B2 | 5/2005 | Khair et al. |
| 6,902,740 B2 | 6/2005 | Schaberg et al. |
| 6,909,878 B2 | 6/2005 | Haller |
| 6,922,592 B2 | 7/2005 | Thompson et al. |
| 6,923,784 B2 | 8/2005 | Stein et al. |
| 6,928,370 B2 | 8/2005 | Anuzis et al. |
| 6,929,636 B1 | 8/2005 | Von Alten |
| 6,937,150 B2 | 8/2005 | Medema |
| 6,941,168 B2 | 9/2005 | Girouard et al. |
| 6,942,616 B2 | 9/2005 | Kerr |
| 6,949,081 B1 | 9/2005 | Chance |
| 6,951,536 B2 | 10/2005 | Yokoi |
| 6,957,107 B2 | 10/2005 | Rogers et al. |
| 6,958,691 B1 | 10/2005 | Anderson et al. |
| 6,959,929 B2 | 11/2005 | Pugnet et al. |
| 6,961,601 B2 * | 11/2005 | Matthews et al. .............. 600/372 |
| 6,968,153 B1 | 11/2005 | Heinonen |
| 6,971,383 B2 | 12/2005 | Hickey et al. |
| 6,981,499 B2 | 1/2006 | Anderson et al. |
| 6,983,652 B2 | 1/2006 | Blakely et al. |
| 6,985,771 B2 | 1/2006 | Fischell et al. |
| 6,985,870 B2 | 1/2006 | Martucci et al. |
| 6,987,965 B2 | 1/2006 | Ng et al. |
| 6,990,082 B1 | 1/2006 | Zehavi et al. |
| 6,990,975 B1 | 1/2006 | Jones et al. |
| 6,999,854 B2 | 2/2006 | Roth |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,010,337 B2 | 3/2006 | Furnary et al. |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,034,692 B2 | 4/2006 | Hickle |
| 7,039,453 B2 | 5/2006 | Mullick |
| 7,040,314 B2 | 5/2006 | Nguyen et al. |
| 7,044,911 B2 | 5/2006 | Drinan et al. |
| 7,046,649 B2 | 5/2006 | Awater et al. |
| 7,047,964 B2 | 5/2006 | Bacon |
| 7,054,782 B2 | 5/2006 | Hartlaub |
| 7,072,802 B2 | 7/2006 | Hartlaub |
| 7,076,437 B1 | 7/2006 | Levy |
| 7,089,935 B1 | 8/2006 | Rand |
| 7,097,853 B1 | 8/2006 | Garbe et al. |
| 7,104,972 B2 | 9/2006 | Moller et al. |
| 7,107,988 B2 | 9/2006 | Pinon et al. |
| 7,108,680 B2 | 9/2006 | Rohr et al. |
| 7,117,867 B2 | 10/2006 | Cox et al. |
| 7,118,531 B2 | 10/2006 | Krill |
| 7,127,300 B2 | 10/2006 | Mazar et al. |
| 7,138,088 B2 | 11/2006 | Wariar et al. |
| 7,146,228 B2 | 12/2006 | Nielsen |
| 7,146,449 B2 | 12/2006 | Do et al. |
| 7,147,170 B2 | 12/2006 | Nguyen et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,168,597 B1 | 1/2007 | Jones et al. |
| 7,171,166 B2 | 1/2007 | Ng et al. |
| 7,171,177 B2 | 1/2007 | Park et al. |
| 7,171,259 B2 | 1/2007 | Rytky |
| 7,181,261 B2 | 2/2007 | Silver et al. |
| 7,187,960 B2 | 3/2007 | Abreu |
| 7,188,767 B2 | 3/2007 | Penuela |
| 7,191,777 B2 | 3/2007 | Brand et al. |
| 7,194,038 B1 | 3/2007 | Inkinen |
| 7,198,172 B2 | 4/2007 | Harvey et al. |
| 7,201,734 B2 | 4/2007 | Hickle |
| 7,204,823 B2 | 4/2007 | Estes et al. |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,220,240 B2 | 5/2007 | Struys et al. |
| 7,225,805 B2 | 6/2007 | Bacon |

(56) References Cited

U.S. PATENT DOCUMENTS

| | | |
|---|---|---|
| 7,231,451 B2 | 6/2007 | Law |
| 7,232,435 B2 | 6/2007 | Hildebrand et al. |
| 7,242,981 B2 | 7/2007 | Ginggen |
| 7,243,118 B2 | 7/2007 | Lou |
| 7,246,521 B2 | 7/2007 | Kim |
| 7,247,154 B2 | 7/2007 | Hickle |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,261,733 B1 | 8/2007 | Brown et al. |
| 7,267,121 B2 | 9/2007 | Ivri et al. |
| 7,270,633 B1 | 9/2007 | Goscha |
| 7,273,454 B2 | 9/2007 | Raymond et al. |
| 7,278,983 B2 | 10/2007 | Ireland et al. |
| 7,285,090 B2 | 10/2007 | Stivoric et al. |
| 7,289,855 B2 | 10/2007 | Nghiem |
| 7,291,126 B2 | 11/2007 | Shekalim |
| 7,291,497 B2 | 11/2007 | Holmes |
| 7,292,139 B2 | 11/2007 | Mazar |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,320,675 B2 | 1/2008 | Pastore et al. |
| 7,322,352 B2 | 1/2008 | Minshull et al. |
| 7,322,355 B2 | 1/2008 | Jones et al. |
| 7,331,340 B2 | 2/2008 | Barney |
| 7,336,929 B2 | 2/2008 | Yasuda |
| 7,342,660 B2 | 3/2008 | Altobelli et al. |
| 7,342,895 B2 | 3/2008 | Serpa |
| 7,346,380 B2 | 3/2008 | Axelgaard et al. |
| 7,347,200 B2 | 3/2008 | Jones et al. |
| 7,347,202 B2 | 3/2008 | Aslin et al. |
| 7,347,851 B1 | 3/2008 | Kriksunov |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,367,968 B2 | 5/2008 | Rosenberg et al. |
| 7,373,196 B2 | 5/2008 | Ryu et al. |
| 7,375,739 B2 | 5/2008 | Robbins |
| 7,376,435 B2 | 5/2008 | McGowan |
| 7,380,550 B2 | 6/2008 | Sexton et al. |
| 7,382,263 B2 | 6/2008 | Danowski et al. |
| 7,383,837 B2 | 6/2008 | Robertson et al. |
| 7,387,121 B2 | 6/2008 | Harvey |
| 7,387,607 B2 | 6/2008 | Holt |
| 7,388,903 B2 | 6/2008 | Godfrey et al. |
| 7,389,088 B2 | 6/2008 | Kim |
| 7,390,311 B2 | 6/2008 | Hildebrand et al. |
| 7,392,015 B1 | 6/2008 | Farlow |
| 7,395,105 B2 | 7/2008 | Schmidt et al. |
| 7,395,106 B2 | 7/2008 | Ryu et al. |
| 7,396,330 B2 | 7/2008 | Banet |
| 7,397,730 B2 | 7/2008 | Skyggebjerg et al. |
| 7,404,968 B2 | 7/2008 | Abrams et al. |
| 7,413,544 B2 | 8/2008 | Kerr |
| 7,414,534 B1 | 8/2008 | Kroll et al. |
| 7,415,242 B1 | 8/2008 | Ngan |
| 7,415,384 B2 | 8/2008 | Hartlaub |
| 7,424,268 B2 | 9/2008 | Diener |
| 7,424,319 B2 | 9/2008 | Muehlsteff |
| 7,424,888 B2 | 9/2008 | Harvey et al. |
| 7,427,266 B2 | 9/2008 | Ayer et al. |
| 7,455,667 B2 | 11/2008 | Uhland et al. |
| 7,458,373 B2 | 12/2008 | Nichols et al. |
| 7,467,629 B2 | 12/2008 | Rand |
| 7,471,665 B2 | 12/2008 | Perlman |
| 7,483,743 B2 | 1/2009 | Mann et al. |
| 7,488,305 B2 | 2/2009 | Mickley et al. |
| 7,495,546 B2 | 2/2009 | Lintell et al. |
| 7,499,674 B2 | 3/2009 | Salokannel |
| 7,502,643 B2 | 3/2009 | Farringdon et al. |
| 7,505,795 B1 | 3/2009 | Lim et al. |
| 7,510,121 B2 | 3/2009 | Koenck |
| 7,510,551 B2 | 3/2009 | Uhland et al. |
| 7,512,448 B2 | 3/2009 | Malick |
| 7,515,043 B2 | 4/2009 | Welch |
| 7,517,332 B2 | 4/2009 | Tonelli et al. |
| 7,520,278 B2 | 4/2009 | Crowder et al. |
| 7,523,756 B2 | 4/2009 | Minai |
| 7,525,426 B2 | 4/2009 | Edelstein |
| 7,530,352 B2 | 5/2009 | Childers et al. |
| 7,530,975 B2 | 5/2009 | Hunter |
| 7,537,590 B2 | 5/2009 | Santini et al. |
| 7,539,533 B2 | 5/2009 | Tran |
| 7,542,798 B2 | 6/2009 | Girouard |
| 7,542,878 B2 | 6/2009 | Nanikashvili |
| 7,544,190 B2 | 6/2009 | Pickup et al. |
| 7,548,314 B2 | 6/2009 | Altobelli et al. |
| 7,549,421 B2 | 6/2009 | Levi et al. |
| 7,551,590 B2 | 6/2009 | Haller |
| 7,552,728 B2 | 6/2009 | Bonney et al. |
| 7,554,090 B2 | 6/2009 | Coleman et al. |
| 7,554,452 B2 | 6/2009 | Cole |
| 7,575,003 B2 | 8/2009 | Rasmussen et al. |
| 7,575,005 B2 | 8/2009 | Mumford |
| 7,581,540 B2 | 9/2009 | Hale et al. |
| 7,597,099 B2 | 10/2009 | Jones et al. |
| 7,616,111 B2 | 11/2009 | Covannon |
| 7,616,710 B2 | 11/2009 | Kim et al. |
| 7,617,001 B2 | 11/2009 | Penner |
| 7,631,643 B2 | 12/2009 | Morrison et al. |
| 7,640,802 B2 | 1/2010 | King |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,668,437 B1 | 2/2010 | Yamada et al. |
| 7,670,329 B2 | 3/2010 | Flaherty et al. |
| 7,672,703 B2 | 3/2010 | Yeo et al. |
| 7,672,714 B2 | 3/2010 | Kuo |
| 7,672,726 B2 | 3/2010 | Ginggen |
| 7,673,679 B2 | 3/2010 | Harrison et al. |
| 7,677,467 B2 | 3/2010 | Fink et al. |
| 7,678,043 B2 | 3/2010 | Gilad |
| 7,686,788 B2 | 3/2010 | Freyman et al. |
| 7,688,204 B2 | 3/2010 | Yamanaka et al. |
| 7,689,437 B1 | 3/2010 | Teller et al. |
| 7,697,994 B2 | 4/2010 | VanDanacker et al. |
| 7,699,060 B2 | 4/2010 | Bahm |
| 7,699,829 B2 | 4/2010 | Harris et al. |
| 7,708,011 B2 | 5/2010 | Hochrainer et al. |
| 7,713,229 B2 | 5/2010 | Veit et al. |
| 7,715,919 B2 | 5/2010 | Osorio et al. |
| 7,717,877 B2 | 5/2010 | Lavi et al. |
| 7,720,036 B2 | 5/2010 | Sadri |
| 7,725,161 B2 | 5/2010 | Karmarkar et al. |
| 7,729,776 B2 | 6/2010 | Von Arx et al. |
| 7,733,224 B2 | 6/2010 | Tran |
| 7,736,318 B2 | 6/2010 | Costentino |
| 7,756,587 B2 | 7/2010 | Penner et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 7,904,133 B2 | 3/2011 | Gehman et al. |
| D639,437 S | 6/2011 | Bishay et al. |
| 8,073,707 B2 | 12/2011 | Teller et al. |
| 8,083,128 B2 | 12/2011 | Dembo et al. |
| 8,123,576 B2 | 2/2012 | Kim |
| 8,170,515 B2 | 5/2012 | Le Reverend et al. |
| 8,180,425 B2 | 5/2012 | Selvitelli et al. |
| 8,193,821 B2 | 6/2012 | Mueller |
| 8,200,320 B2 | 6/2012 | Kovacs |
| 8,214,007 B2 | 7/2012 | Baker et al. |
| 8,238,998 B2 | 8/2012 | Park |
| 8,249,686 B2 | 8/2012 | Libbus et al. |
| 8,285,356 B2 | 10/2012 | Bly et al. |
| 8,290,574 B2 | 10/2012 | Feild et al. |
| 8,301,232 B2 | 10/2012 | Albert et al. |
| 8,308,640 B2 | 11/2012 | Baldus et al. |
| 8,315,687 B2 | 11/2012 | Cross et al. |

(56) References Cited

U.S. PATENT DOCUMENTS

| | | |
|---|---|---|
| 8,332,009 B2 | 12/2012 | McLaughlin et al. |
| 8,369,936 B2 | 2/2013 | Farringdon et al. |
| 8,386,009 B2 | 2/2013 | Lindberg et al. |
| 8,440,274 B2 | 5/2013 | Wang |
| 2001/0000802 A1 | 5/2001 | Soykan et al. |
| 2001/0022279 A1 | 9/2001 | Denyer et al. |
| 2001/0027331 A1 | 10/2001 | Thompson |
| 2001/0031071 A1 | 10/2001 | Nichols et al. |
| 2001/0044588 A1 | 11/2001 | Mault |
| 2001/0051766 A1 | 12/2001 | Gazdinski |
| 2001/0056262 A1 | 12/2001 | Cabiri et al. |
| 2002/0000225 A1 | 1/2002 | Schuler et al. |
| 2002/0002326 A1 | 1/2002 | Causey et al. |
| 2002/0002349 A1 | 1/2002 | Flaherty et al. |
| 2002/0010432 A1 | 1/2002 | Klitmose et al. |
| 2002/0013615 A1 | 1/2002 | Haim et al. |
| 2002/0026111 A1 | 2/2002 | Ackerman |
| 2002/0026940 A1 | 3/2002 | Brooker et al. |
| 2002/0040278 A1 | 4/2002 | Anuzis et al. |
| 2002/0077620 A1 | 6/2002 | Sweeney et al. |
| 2002/0077852 A1 | 6/2002 | Ford et al. |
| 2002/0099328 A1 | 7/2002 | Scheiner et al. |
| 2002/0120236 A1 | 8/2002 | Diaz et al. |
| 2002/0132226 A1 | 9/2002 | Nair |
| 2002/0153006 A1 | 10/2002 | Zimlich et al. |
| 2002/0189612 A1 | 12/2002 | Rand et al. |
| 2002/0189615 A1 | 12/2002 | Henry et al. |
| 2002/0192159 A1 | 12/2002 | Reitberg |
| 2002/0193669 A1 | 12/2002 | Glukhovsky |
| 2002/0198470 A1 | 12/2002 | Imran et al. |
| 2002/0198493 A1 | 12/2002 | Diaz et al. |
| 2003/0004236 A1 | 1/2003 | Meade et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0065536 A1 | 4/2003 | Hansen |
| 2003/0076179 A1 | 4/2003 | Branch et al. |
| 2003/0078561 A1 | 4/2003 | Gambale et al. |
| 2003/0079744 A1 | 5/2003 | Bonney et al. |
| 2003/0083559 A1 | 5/2003 | Thompson |
| 2003/0094508 A1 | 5/2003 | Peng et al. |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0136418 A1 | 7/2003 | Behm et al. |
| 2003/0140921 A1 | 7/2003 | Smith et al. |
| 2003/0150446 A1 | 8/2003 | Patel et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0159693 A1 | 8/2003 | Melker et al. |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0168057 A1 | 9/2003 | Snyder et al. |
| 2003/0171738 A1 | 9/2003 | Konieczynski et al. |
| 2003/0171791 A1 | 9/2003 | KenKnight |
| 2003/0171898 A1 | 9/2003 | Tarassenko et al. |
| 2003/0176804 A1 | 9/2003 | Melker et al. |
| 2003/0181788 A1 | 9/2003 | Yokoi et al. |
| 2003/0181815 A1 | 9/2003 | Ebner et al. |
| 2003/0183226 A1 | 10/2003 | Brand et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0205229 A1 | 11/2003 | Crockford et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0229382 A1 | 12/2003 | Sun et al. |
| 2004/0004133 A1 | 1/2004 | Ivri et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0019321 A1 | 1/2004 | Sage et al. |
| 2004/0025871 A1 | 2/2004 | Davies et al. |
| 2004/0031331 A1 | 2/2004 | Blakely et al. |
| 2004/0034295 A1 | 2/2004 | Salganicoff |
| 2004/0049245 A1 | 3/2004 | Gass |
| 2004/0050385 A1 | 3/2004 | Bonney et al. |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0089299 A1 | 5/2004 | Bonney et al. |
| 2004/0092801 A1 | 5/2004 | Drakulic |
| 2004/0098117 A1 | 5/2004 | Hossainy et al. |
| 2004/0106859 A1 | 6/2004 | Say et al. |
| 2004/0106902 A1 | 6/2004 | Diaz et al. |
| 2004/0115517 A1 | 6/2004 | Fukuda et al. |
| 2004/0121015 A1 | 6/2004 | Chidlaw et al. |
| 2004/0122297 A1 | 6/2004 | Stahmann et al. |
| 2004/0122530 A1 | 6/2004 | Hansen et al. |
| 2004/0133154 A1 | 7/2004 | Flaherty et al. |
| 2004/0139963 A1 | 7/2004 | Ivri et al. |
| 2004/0148140 A1 | 7/2004 | Tarassenko et al. |
| 2004/0153007 A1 | 8/2004 | Harris |
| 2004/0158167 A1* | 8/2004 | Smith et al. .................. 600/547 |
| 2004/0167226 A1 | 8/2004 | Serafini |
| 2004/0167801 A1 | 8/2004 | Say et al. |
| 2004/0181196 A1 | 9/2004 | Pickup et al. |
| 2004/0187864 A1 | 9/2004 | Adams et al. |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0193453 A1 | 9/2004 | Butterfield et al. |
| 2004/0199222 A1 | 10/2004 | Sun et al. |
| 2004/0210199 A1 | 10/2004 | Atterbury et al. |
| 2004/1215084 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0254435 A1 | 12/2004 | Mathews et al. |
| 2004/0260154 A1 | 12/2004 | Sidelnik |
| 2005/0010166 A1 | 1/2005 | Hickle |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0045734 A1 | 3/2005 | Peng et al. |
| 2005/0055014 A1 | 3/2005 | Coppeta et al. |
| 2005/0059924 A1 | 3/2005 | Katz et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0072421 A1 | 4/2005 | Suman et al. |
| 2005/0081845 A1 | 4/2005 | Barney et al. |
| 2005/0087189 A1 | 4/2005 | Crockford et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0137626 A1 | 6/2005 | Pastore et al. |
| 2005/0139651 A1 | 6/2005 | Lim |
| 2005/0143623 A1 | 6/2005 | Kojima |

(56) References Cited

U.S. PATENT DOCUMENTS

| | | |
|---|---|---|
| 2005/0148883 A1 | 7/2005 | Boesen |
| 2005/0154428 A1 | 7/2005 | Bruinsma |
| 2005/0155602 A1 | 7/2005 | Lipp |
| 2005/0165323 A1 | 7/2005 | Montgomery |
| 2005/0165342 A1 | 7/2005 | Odland |
| 2005/0172956 A1 | 8/2005 | Childers et al. |
| 2005/0172958 A1 | 8/2005 | Singer et al. |
| 2005/0177069 A1 | 8/2005 | Takizawa |
| 2005/0182389 A1 | 8/2005 | LaPorte |
| 2005/0183725 A1 | 8/2005 | Gumaste et al. |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0203637 A1 | 9/2005 | Edman et al. |
| 2005/0228268 A1 | 10/2005 | Cole |
| 2005/0234307 A1 | 10/2005 | Heinonen |
| 2005/0235732 A1 | 10/2005 | Rush |
| 2005/0236501 A1 | 10/2005 | Zimlich et al. |
| 2005/0240305 A1 | 10/2005 | Bogash et al. |
| 2005/0245794 A1 | 11/2005 | Dinsmoor |
| 2005/0245906 A1 | 11/2005 | Makower et al. |
| 2005/0247312 A1 | 11/2005 | Davies |
| 2005/0251289 A1 | 11/2005 | Bonney et al. |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0274378 A1 | 12/2005 | Bonney et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0005842 A1 | 1/2006 | Rashad et al. |
| 2006/0030813 A1 | 2/2006 | Chance |
| 2006/0031099 A1 | 2/2006 | Vitello et al. |
| 2006/0036134 A1 | 2/2006 | Tarassenko et al. |
| 2006/0037612 A1 | 2/2006 | Herder et al. |
| 2006/0042632 A1 | 3/2006 | Bishop et al. |
| 2006/0058593 A1 | 3/2006 | Drinan et al. |
| 2006/0061472 A1 | 3/2006 | Lovoi et al. |
| 2006/0065713 A1 | 3/2006 | Kingery |
| 2006/0074283 A1 | 4/2006 | Henderson |
| 2006/0078765 A1 | 4/2006 | Yang et al. |
| 2006/0090752 A1 | 5/2006 | Imondi et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0130832 A1 | 6/2006 | Schechter et al. |
| 2006/0131350 A1 | 6/2006 | Schechter et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0167530 A1 | 7/2006 | Flaherty et al. |
| 2006/0178586 A1 | 8/2006 | Dobak |
| 2006/0179949 A1 | 8/2006 | Kim |
| 2006/0183993 A1 | 8/2006 | Horn |
| 2006/0184087 A1 | 8/2006 | Wariar et al. |
| 2006/0184092 A1 | 8/2006 | Atanasoska et al. |
| 2006/0191534 A1 | 8/2006 | Hickey et al. |
| 2006/0201499 A1 | 9/2006 | Muellinger et al. |
| 2006/0204532 A1 | 9/2006 | John et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0231093 A1 | 10/2006 | Burge et al. |
| 2006/0235489 A1 | 10/2006 | Drew |
| 2006/0243277 A1 | 11/2006 | Denyer et al. |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0255064 A1 | 11/2006 | Donaldson |
| 2006/0265246 A1 | 11/2006 | Hoag |
| 2006/0270346 A1 | 11/2006 | Ibrahim |
| 2006/0280227 A1 | 12/2006 | Pinkney |
| 2006/0282001 A1 | 12/2006 | Noel |
| 2006/0283465 A1 | 12/2006 | Nickel et al. |
| 2006/0289640 A1 | 12/2006 | Mercure |
| 2006/0293607 A1 | 12/2006 | Alt |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0023034 A1 | 2/2007 | Jongejan et al. |
| 2007/0023036 A1 | 2/2007 | Grychowski et al. |
| 2007/0027386 A1 | 2/2007 | Such |
| 2007/0027388 A1 | 2/2007 | Chou |
| 2007/0038054 A1 | 2/2007 | Zhou |
| 2007/0043591 A1 | 2/2007 | Meretei et al. |
| 2007/0044793 A1 | 3/2007 | Kleinstreuer et al. |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0073353 A1 | 3/2007 | Rooney et al. |
| 2007/0074722 A1 | 4/2007 | Giroux et al. |
| 2007/0088334 A1 | 4/2007 | Hillis et al. |
| 2007/0091273 A1 | 4/2007 | Sullivan et al. |
| 2007/0096765 A1 | 5/2007 | Kagan |
| 2007/0106346 A1 | 5/2007 | Bergelson |
| 2007/0107517 A1 | 5/2007 | Arnold et al. |
| 2007/0123772 A1 | 5/2007 | Euliano |
| 2007/0123829 A1 | 5/2007 | Atterbury et al. |
| 2007/0125370 A1 | 6/2007 | Denyer et al. |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0157931 A1 | 7/2007 | Parker et al. |
| 2007/0161879 A1 | 7/2007 | Say et al. |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0169778 A1 | 7/2007 | Smith et al. |
| 2007/0173701 A1 | 7/2007 | Al-Ali |
| 2007/0179347 A1 | 8/2007 | Tarassenko et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |
| 2007/0197954 A1 | 8/2007 | Keenan |
| 2007/0203411 A1 | 8/2007 | Say et al. |
| 2007/0207793 A1 | 9/2007 | Myer |
| 2007/0208233 A1 | 9/2007 | Kovacs |
| 2007/0208322 A1 | 9/2007 | Rantala et al. |
| 2007/0209659 A1 | 9/2007 | Ivri et al. |
| 2007/0213658 A1 | 9/2007 | Hickle |
| 2007/0213659 A1 | 9/2007 | Trovato et al. |
| 2007/0221218 A1 | 9/2007 | Warden et al. |
| 2007/0224128 A1 | 9/2007 | Dennis et al. |
| 2007/0237719 A1 | 10/2007 | Jones |
| 2007/0240712 A1 | 10/2007 | Fleming et al. |
| 2007/0244370 A1 | 10/2007 | Kuo et al. |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0256688 A1 | 11/2007 | Schuster et al. |
| 2007/0258894 A1 | 11/2007 | Melker et al. |
| 2007/0270672 A1 | 11/2007 | Hayter |
| 2007/0279217 A1 | 12/2007 | Venkatraman |
| 2007/0282174 A1 | 12/2007 | Sabatino |

(56) References Cited

U.S. PATENT DOCUMENTS

| | | |
|---|---|---|
| 2007/0282177 A1 | 12/2007 | Pilz |
| 2007/0291715 A1 | 12/2007 | Laroia et al. |
| 2007/0295329 A1 | 12/2007 | Lieberman et al. |
| 2007/0299480 A1 | 12/2007 | Hill |
| 2007/0299550 A1 | 12/2007 | Nishijima et al. |
| 2008/0009800 A1 | 1/2008 | Nickel |
| 2008/0014866 A1 | 1/2008 | Lipowski |
| 2008/0015421 A1 | 1/2008 | Penner |
| 2008/0015494 A1 | 1/2008 | Santini et al. |
| 2008/0020037 A1 | 1/2008 | Robertson et al. |
| 2008/0021379 A1 | 1/2008 | Hickle |
| 2008/0021519 A1 | 1/2008 | De Geest |
| 2008/0021521 A1 | 1/2008 | Shah |
| 2008/0027679 A1 | 1/2008 | Shklarski |
| 2008/0033273 A1 | 2/2008 | Zhou |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051667 A1 | 2/2008 | Goldreich |
| 2008/0051767 A1 | 2/2008 | Rossing et al. |
| 2008/0058614 A1 | 3/2008 | Banet |
| 2008/0058703 A1 | 3/2008 | Subramony et al. |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077080 A1 | 3/2008 | Hengstenberg et al. |
| 2008/0077188 A1 | 3/2008 | Denker et al. |
| 2008/0078382 A1 | 4/2008 | LeMahieu et al. |
| 2008/0078385 A1 | 4/2008 | Xiao et al. |
| 2008/0082001 A1 | 4/2008 | Hatlestad et al. |
| 2008/0086112 A1 | 4/2008 | Lo et al. |
| 2008/0091089 A1 | 4/2008 | Guillory et al. |
| 2008/0091114 A1 | 4/2008 | Min |
| 2008/0091138 A1 | 4/2008 | Pastore et al. |
| 2008/0097549 A1 | 4/2008 | Colbaugh |
| 2008/0097917 A1 | 4/2008 | Dicks |
| 2008/0099366 A1 | 5/2008 | Niemic et al. |
| 2008/0103440 A1 | 5/2008 | Ferren et al. |
| 2008/0114224 A1 | 5/2008 | Bandy et al. |
| 2008/0114299 A1 | 5/2008 | Damgaard-Sorensen et al. |
| 2008/0119705 A1 | 5/2008 | Patel |
| 2008/0119716 A1 | 5/2008 | Boric-Lubecke |
| 2008/0125759 A1 | 5/2008 | Konieczynski et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0142002 A1 | 6/2008 | Fink et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0147004 A1 | 6/2008 | Mann et al. |
| 2008/0147050 A1 | 6/2008 | Mann et al. |
| 2008/0154104 A1 | 6/2008 | Lamego |
| 2008/0166992 A1 | 7/2008 | Ricordi |
| 2008/0173301 A1 | 7/2008 | Deaton et al. |
| 2008/0177246 A1 | 7/2008 | Sullivan et al. |
| 2008/0178872 A1 | 7/2008 | Genova et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0200804 A1 | 8/2008 | Hartlep et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0216834 A1 | 9/2008 | Easley et al. |
| 2008/0221408 A1 | 9/2008 | Hoarau et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0262469 A1 | 10/2008 | Brister et al. |
| 2008/0269664 A1 | 10/2008 | Trovato et al. |
| 2008/0269689 A1 | 10/2008 | Edwards et al. |
| 2008/0275312 A1 | 11/2008 | Mosesov |
| 2008/0281276 A1 | 11/2008 | Shekalim |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0306362 A1 | 12/2008 | Davis |
| 2008/0306436 A1 | 12/2008 | Edwards et al. |
| 2008/0306444 A1 | 12/2008 | Brister et al. |
| 2008/0306449 A1 | 12/2008 | Kristensen et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0005763 A1 | 1/2009 | Makower et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0025714 A1 | 1/2009 | Denyer et al. |
| 2009/0025718 A1 | 1/2009 | Denyer et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0048526 A1 | 2/2009 | Aarts et al. |
| 2009/0048556 A1 | 2/2009 | Durand |
| 2009/0056708 A1 | 3/2009 | Stenzler |
| 2009/0062634 A1 | 3/2009 | Say et al. |
| 2009/0062670 A1 | 3/2009 | Sterling |
| 2009/0064997 A1 | 3/2009 | Li |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076397 A1 | 3/2009 | Libbus et al. |
| 2009/0082645 A1 | 3/2009 | Hafezi et al. |
| 2009/0082829 A1 | 3/2009 | Panken et al. |
| 2009/0088618 A1 | 4/2009 | Ameson |
| 2009/0099435 A1 | 4/2009 | Say et al. |
| 2009/0107503 A1 | 4/2009 | Baran |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0151718 A1 | 6/2009 | Hunter et al. |
| 2009/0156952 A1 | 6/2009 | Hunter et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163781 A1 | 6/2009 | Say et al. |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |

(56) References Cited

U.S. PATENT DOCUMENTS

| | | |
|---|---|---|
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187167 A1 | 7/2009 | Sexton et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0194104 A1 | 8/2009 | Van Sickle |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0211576 A1 | 8/2009 | Lehtonen et al. |
| 2009/0213373 A1 | 8/2009 | Altobelli et al. |
| 2009/0216101 A1 | 8/2009 | Say et al. |
| 2009/0216102 A1 | 8/2009 | Say et al. |
| 2009/0216194 A1 | 8/2009 | Elgard et al. |
| 2009/0221087 A1 | 9/2009 | Martin et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0228214 A1 | 9/2009 | Say et al. |
| 2009/0229607 A1 | 9/2009 | Brunnberg et al. |
| 2009/0231125 A1 | 9/2009 | Baldus |
| 2009/0234200 A1 | 9/2009 | Husheer |
| 2009/0241951 A1 | 10/2009 | Jafari et al. |
| 2009/0241955 A1 | 10/2009 | Jafari et al. |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0270752 A1 | 10/2009 | Coifman |
| 2009/0273467 A1 | 11/2009 | Elixmann |
| 2009/0281539 A1 | 11/2009 | Selig |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301472 A1 | 12/2009 | Kim et al. |
| 2009/0301925 A1 | 12/2009 | Alloro et al. |
| 2009/0303920 A1 | 12/2009 | Mahany |
| 2009/0312619 A1 | 12/2009 | Say et al. |
| 2009/0314372 A1 | 12/2009 | Ruskewicz et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2009/0326509 A1 | 12/2009 | Muse et al. |
| 2009/0326510 A1 | 12/2009 | Haefner et al. |
| 2010/0010330 A1 | 1/2010 | Rankers |
| 2010/0012120 A1 | 1/2010 | Herder et al. |
| 2010/0031957 A1 | 2/2010 | McIntosh |
| 2010/0033324 A1 | 2/2010 | Shimizu et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0049172 A1 | 2/2010 | Chance |
| 2010/0049263 A1 | 2/2010 | Reeve |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0078015 A1 | 4/2010 | Imran |
| 2010/0081894 A1 | 4/2010 | Zdeblick et al. |
| 2010/0094099 A1 | 4/2010 | Levy et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0100160 A1 | 4/2010 | Edman et al. |
| 2010/0106001 A1 | 4/2010 | Say et al. |
| 2010/0106098 A1 | 4/2010 | Atterbury et al. |
| 2010/0114026 A1 | 5/2010 | Karratt et al. |
| 2010/0114060 A1 | 5/2010 | Ginggen et al. |
| 2010/0116070 A1 | 5/2010 | Farina et al. |
| 2010/0118853 A1 | 5/2010 | Godfrey |
| 2010/0121314 A1 | 5/2010 | Iobbi |
| 2010/0122697 A1 | 5/2010 | Przekwas et al. |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0185055 A1 | 7/2010 | Robertson |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0268111 A1 | 10/2010 | Drinan et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0298730 A1 | 11/2010 | Tarassenko et al. |
| 2010/0312188 A1 | 12/2010 | Robertson et al. |
| 2010/0312580 A1 | 12/2010 | Tarassenko et al. |
| 2011/0004079 A1 | 1/2011 | Al Ali et al. |
| 2011/0040203 A1 | 2/2011 | Savage et al. |
| 2011/0065983 A1 | 3/2011 | Hafezi et al. |
| 2011/0081860 A1 | 4/2011 | Brown et al. |
| 2011/0124983 A1 | 5/2011 | Kroll et al. |
| 2011/0144470 A1 | 6/2011 | Mazar et al. |
| 2011/0224912 A1 | 9/2011 | Bhavaraju et al. |
| 2011/0230732 A1 | 9/2011 | Edman et al. |
| 2011/0237924 A1 | 9/2011 | McGusty et al. |
| 2011/0279963 A1 | 11/2011 | Kumar et al. |
| 2012/0029309 A1 | 2/2012 | Paquet et al. |
| 2012/0083715 A1 | 4/2012 | Yuen et al. |
| 2012/0089000 A1 | 4/2012 | Bishay et al. |
| 2012/0101396 A1 | 4/2012 | Solosko et al. |
| 2012/0197144 A1 | 8/2012 | Christ et al. |
| 2012/0310070 A1 | 12/2012 | Kumar et al. |
| 2012/0316413 A1 | 12/2012 | Liu et al. |
| 2013/0030259 A1 | 1/2013 | Thompsen et al. |

(56) References Cited

U.S. PATENT DOCUMENTS

| | | | |
|---|---|---|---|
| 2013/0057385 A1 | 3/2013 | Murakami et al. | |
| 2013/0060115 A1 | 3/2013 | Gehman et al. | |

FOREIGN PATENT DOCUMENTS

| | | |
|---|---|---|
| EP | 1246356 | 10/2002 |
| EP | 1789128 | 5/2007 |
| EP | 2143369 | 1/2010 |
| JP | 361017949 | 1/1986 |
| JP | 61072712 | 4/1986 |
| JP | S62112529 | 5/1987 |
| JP | 05-228128 | 9/1993 |
| JP | 6296633 | 10/1994 |
| JP | 10-14898 | 1/1998 |
| JP | 2000-506410 | 5/2000 |
| JP | 2001-061799 | 3/2001 |
| JP | 2002-224053 | 8/2002 |
| JP | 2002291684 | 10/2002 |
| JP | 2004-7187 | 1/2004 |
| JP | 2004-313242 | 11/2004 |
| JP | 2005-304880 | 4/2005 |
| JP | 2005-532841 | 11/2005 |
| JP | 2005-532849 | 11/2005 |
| JP | 2006508752 | 3/2006 |
| JP | 2006509574 | 3/2006 |
| JP | 2006-177699 | 7/2006 |
| JP | 2008011865 | 1/2008 |
| JP | 2008501415 | 1/2008 |
| JP | 2008086390 | 4/2008 |
| JP | 2008-525063 | 7/2008 |
| JP | 2008191110 | 8/2008 |
| KR | 10-2012-09995 | 9/2012 |
| TW | 553735 | 9/2003 |
| TW | 200724094 | 7/2007 |
| WO | WO 8102982 | 10/1981 |
| WO | WO 8607269 | 12/1986 |
| WO | WO 8802237 | 4/1988 |
| WO | WO 9207599 | 5/1992 |
| WO | WO 9209324 | 6/1992 |
| WO | WO 9211808 | 7/1992 |
| WO | WO 9215353 | 9/1992 |
| WO | WO 9217231 | 10/1992 |
| WO | WO 9306803 | 4/1993 |
| WO | WO 9308734 | 5/1993 |
| WO | WO 9312823 | 7/1993 |
| WO | WO 9319667 | 10/1993 |
| WO | WO 9405359 | 3/1994 |
| WO | WO 9408655 | 4/1994 |
| WO | WO 9416755 | 8/1994 |
| WO | WO 9416756 | 8/1994 |
| WO | WO 9416759 | 8/1994 |
| WO | WO 9427653 | 12/1994 |
| WO | WO 9507723 | 3/1995 |
| WO | WO 9507724 | 3/1995 |
| WO | WO 9513838 | 5/1995 |
| WO | WO 9526769 | 10/1995 |
| WO | WO 9610440 | 4/1996 |
| WO | WO 9616686 | 6/1996 |
| WO | WO 9625186 | 8/1996 |
| WO | WO 9625978 | 8/1996 |
| WO | WO 9627341 | 9/1996 |
| WO | WO 9630078 | 10/1996 |
| WO | WO 9707896 | 3/1997 |
| WO | WO 9711655 | 4/1997 |
| WO | WO 9711742 | 4/1997 |
| WO | WO 9711743 | 4/1997 |
| WO | WO9714112 | 4/1997 |
| WO | WO 9726934 | 7/1997 |
| WO | WO 9733640 | 9/1997 |
| WO | WO 9733645 | 9/1997 |
| WO | WO 9748431 | 12/1997 |
| WO | WO 9800188 | 1/1998 |
| WO | WO 9801168 | 1/1998 |
| WO | WO 9806450 | 2/1998 |
| WO | WO 9814235 | 4/1998 |
| WO | WO 9832479 | 7/1998 |
| WO | WO 9839057 | 9/1998 |
| WO | WO 9843537 | 10/1998 |
| WO | WO 9844984 | 10/1998 |
| WO | WO 9850095 | 11/1998 |
| WO | WO 9900144 | 1/1999 |
| WO | WO 9930760 | 6/1999 |
| WO | WO 9959465 | 11/1999 |
| WO | WO 9965551 | 12/1999 |
| WO | WO 0001434 | 1/2000 |
| WO | WO 0007652 | 2/2000 |
| WO | WO 0018339 | 4/2000 |
| WO | WO 0021598 | 4/2000 |
| WO | WO 0027278 | 5/2000 |
| WO | WO 0032267 | 6/2000 |
| WO | WO 0033246 | 6/2000 |
| WO | WO 0038770 | 7/2000 |
| WO | WO 0043059 | 7/2000 |
| WO | WO 0047253 | 8/2000 |
| WO | WO 0050111 | 8/2000 |
| WO | WO 0053247 | 9/2000 |
| WO | WO 0059483 | 10/2000 |
| WO | WO 0100085 | 1/2001 |
| WO | WO 0105463 | 1/2001 |
| WO | WO 0113973 | 3/2001 |
| WO | WO 0124851 | 4/2001 |
| WO | WO 0130419 | 5/2001 |
| WO | WO 0147466 | 7/2001 |
| WO | WO 0158236 | 8/2001 |
| WO | WO 0168169 | 9/2001 |
| WO | WO 0174011 | 10/2001 |
| WO | WO 0180731 | 11/2001 |
| WO | WO 0183007 | 11/2001 |
| WO | WO 0185027 | 11/2001 |
| WO | WO 0187378 | 11/2001 |
| WO | WO 0189607 | 11/2001 |
| WO | WO 0200280 | 1/2002 |
| WO | WO 0202052 | 1/2002 |
| WO | WO 0204043 | 1/2002 |
| WO | WO 0217988 | 3/2002 |
| WO | WO 0217998 | 3/2002 |
| WO | WO 0224257 | 3/2002 |
| WO | WO 0224268 | 3/2002 |
| WO | WO 0234318 | 5/2002 |
| WO | WO 0236181 | 5/2002 |
| WO | WO 0245489 | 6/2002 |
| WO | WO 02053223 | 7/2002 |
| WO | WO 02058330 | 7/2002 |
| WO | WO 02062276 | 8/2002 |
| WO | WO 02072178 | 9/2002 |
| WO | WO 02076533 | 10/2002 |
| WO | WO 02078535 | 10/2002 |
| WO | WO 02081016 | 10/2002 |
| WO | WO 02087681 | 11/2002 |
| WO | WO 02089879 | 11/2002 |
| WO | WO 02089884 | 11/2002 |
| WO | WO 02096489 | 12/2002 |
| WO | WO 03006091 | 1/2003 |
| WO | WO 03008014 | 1/2003 |
| WO | WO 03020349 | 3/2003 |
| WO | WO 03022327 | 3/2003 |
| WO | WO 03028797 | 4/2003 |
| WO | WO 03035172 | 5/2003 |
| WO | WO 03038566 | 5/2003 |
| WO | WO 03045302 | 6/2003 |
| WO | WO 03050643 | 6/2003 |
| WO | WO 03059413 | 7/2003 |
| WO | WO 03071930 | 9/2003 |
| WO | WO 03073977 | 9/2003 |
| WO | WO 03086505 | 10/2003 |
| WO | WO 03090821 | 11/2003 |
| WO | WO 03097120 | 11/2003 |
| WO | WO 2004009161 | 1/2004 |
| WO | WO 2004011067 | 2/2004 |
| WO | WO 2004012801 | 2/2004 |
| WO | WO 2004014225 | 2/2004 |
| WO | WO 2004020024 | 3/2004 |
| WO | WO 2004021882 | 3/2004 |

(56) References Cited

FOREIGN PATENT DOCUMENTS

| | | |
|---|---|---|
| WO | WO 2004022128 | 3/2004 |
| WO | WO 2004022153 | 3/2004 |
| WO | WO 2004022242 | 3/2004 |
| WO | WO 2004026380 | 4/2004 |
| WO | WO 2004032989 | 4/2004 |
| WO | WO 2004034998 | 4/2004 |
| WO | WO 2004039256 | 5/2004 |
| WO | WO 2004041334 | 5/2004 |
| WO | WO 2004041339 | 5/2004 |
| WO | WO 2004045690 | 6/2004 |
| WO | WO2004059551 | 7/2004 |
| WO | WO 2004060436 | 7/2004 |
| WO | WO 2004060443 | 7/2004 |
| WO | WO 2004060447 | 7/2004 |
| WO | WO 2004066834 | 8/2004 |
| WO | WO2004068748 | 8/2004 |
| WO | WO 2004068881 | 8/2004 |
| WO | WO2004075751 | 9/2004 |
| WO | WO 2004080522 | 9/2004 |
| WO | WO 2004088567 | 10/2004 |
| WO | WO 2004109316 | 12/2004 |
| WO | WO 2005009514 | 2/2005 |
| WO | WO 2005011237 | 2/2005 |
| WO | WO 2005011779 | 2/2005 |
| WO | WO 2005020023 | 3/2005 |
| WO | WO 2005024687 | 3/2005 |
| WO | WO 2005028008 | 3/2005 |
| WO | WO 2005031317 | 4/2005 |
| WO | WO 2005039750 | 5/2005 |
| WO | WO2005041767 | 5/2005 |
| WO | WO 2005046559 | 5/2005 |
| WO | WO 2005047837 | 5/2005 |
| WO | WO 2005051166 | 6/2005 |
| WO | WO 2005051177 | 6/2005 |
| WO | WO 2005072798 | 8/2005 |
| WO | WO2005082436 | 9/2005 |
| WO | WO 2005084275 | 9/2005 |
| WO | WO 2005084738 | 9/2005 |
| WO | WO 2005087299 | 9/2005 |
| WO | WO 2005102412 | 11/2005 |
| WO | WO 2005102417 | 11/2005 |
| WO | WO 2005102418 | 11/2005 |
| WO | WO 2005102428 | 11/2005 |
| WO | WO 2005110238 | 11/2005 |
| WO | WO 2005120615 | 12/2005 |
| WO | WO 2005123002 | 12/2005 |
| WO | WO 2006003665 | 1/2006 |
| WO | WO 2006009596 | 1/2006 |
| WO | WO 2006015299 | 2/2006 |
| WO | WO 2006022714 | 3/2006 |
| WO | WO 2006023644 | 3/2006 |
| WO | WO 2006027586 | 3/2006 |
| WO | WO 2006029090 | 3/2006 |
| WO | WO2006035351 | 4/2006 |
| WO | WO 2006035443 | 4/2006 |
| WO | WO 2006044206 | 4/2006 |
| WO | WO 2006045524 | 5/2006 |
| WO | WO2006046648 | 5/2006 |
| WO | WO 2006055892 | 5/2006 |
| WO | WO 2006055956 | 5/2006 |
| WO | WO 2006058426 | 6/2006 |
| WO | WO 2006060106 | 6/2006 |
| WO | WO2006066566 | 6/2006 |
| WO | WO 2006069323 | 6/2006 |
| WO | WO 2006075016 | 7/2006 |
| WO | WO 2006079898 | 8/2006 |
| WO | WO 2006096286 | 9/2006 |
| WO | WO 2006098933 | 9/2006 |
| WO | WO 2006098936 | 9/2006 |
| WO | WO 2006100620 | 9/2006 |
| WO | WO 2006109072 | 10/2006 |
| WO | WO 2006113408 | 10/2006 |
| WO | WO 2006116718 | 11/2006 |
| WO | WO2006119345 | 11/2006 |
| WO | WO 2006120253 | 11/2006 |
| WO | WO 2006124759 | 11/2006 |
| WO | WO 2006125577 | 11/2006 |
| WO | WO 2006127257 | 11/2006 |
| WO | WO 2006127355 | 11/2006 |
| WO | WO 2006127905 | 11/2006 |
| WO | WO 2006127953 | 11/2006 |
| WO | WO 2006128794 | 12/2006 |
| WO | WO 2006130098 | 12/2006 |
| WO | WO 2006133101 | 12/2006 |
| WO | WO 2007001724 | 1/2007 |
| WO | WO 2007001742 | 1/2007 |
| WO | WO 2007012854 | 2/2007 |
| WO | WO 2007013952 | 2/2007 |
| WO | WO 2007014084 | 2/2007 |
| WO | WO 2007014527 | 2/2007 |
| WO | WO 2007021496 | 2/2007 |
| WO | WO 2007027660 | 3/2007 |
| WO | WO 2007028035 | 3/2007 |
| WO | WO 2007031740 | 3/2007 |
| WO | WO 2007034237 | 3/2007 |
| WO | WO 2007036687 | 4/2007 |
| WO | WO 2007036741 | 4/2007 |
| WO | WO 2007036746 | 4/2007 |
| WO | WO 2007040878 | 4/2007 |
| WO | WO 2007041158 | 4/2007 |
| WO | WO 2007041471 | 4/2007 |
| WO | WO 2007051563 | 5/2007 |
| WO | WO 2007070093 | 6/2007 |
| WO | WO 2007070695 | 6/2007 |
| WO | WO 2007071180 | 6/2007 |
| WO | WO 2007096810 | 8/2007 |
| WO | WO 2007101141 | 9/2007 |
| WO | WO 2007120884 | 10/2007 |
| WO | WO 2007120946 | 10/2007 |
| WO | WO 2007125699 | 11/2007 |
| WO | WO 2007127316 | 11/2007 |
| WO | WO 2007127879 | 11/2007 |
| WO | WO 2007127981 | 11/2007 |
| WO | WO 2007128165 | 11/2007 |
| WO | WO 2007130491 | 11/2007 |
| WO | WO 2007131025 | 11/2007 |
| WO | WO 2007143535 | 12/2007 |
| WO | WO 2007149546 | 12/2007 |
| WO | WO 2006104843 | 1/2008 |
| WO | WO 2008008281 | 1/2008 |
| WO | WO 2008016698 | 2/2008 |
| WO | WO 2008021252 | 2/2008 |
| WO | WO 2008022010 | 2/2008 |
| WO | WO 2008029403 | 3/2008 |
| WO | WO 2008030482 | 3/2008 |
| WO | WO 2008030837 | 3/2008 |
| WO | WO 2008037801 | 4/2008 |
| WO | WO 2008038241 | 4/2008 |
| WO | WO 2008039091 | 4/2008 |
| WO | WO 2008043724 | 4/2008 |
| WO | WO 2008052039 | 5/2008 |
| WO | WO 2008052136 | 5/2008 |
| WO | WO 2008063626 | 5/2008 |
| WO | WO 2008066617 | 6/2008 |
| WO | WO 2008073806 | 6/2008 |
| WO | WO 2008076464 | 6/2008 |
| WO | WO 2008077706 | 7/2008 |
| WO | WO 2008078287 | 7/2008 |
| WO | WO 2008089232 | 7/2008 |
| WO | WO 2008091683 | 7/2008 |
| WO | WO 2008095183 | 8/2008 |
| WO | WO 2008097652 | 8/2008 |
| WO | WO 2008101107 | 8/2008 |
| WO | WO 2008103620 | 8/2008 |
| WO | WO 2008112577 | 9/2008 |
| WO | WO 2008112578 | 9/2008 |
| WO | WO 2008115906 | 9/2008 |
| WO | WO 2008117226 | 10/2008 |
| WO | WO 2008120156 | 10/2008 |
| WO | WO 2008127743 | 10/2008 |
| WO | WO 2008130801 | 10/2008 |
| WO | WO 2008133394 | 11/2008 |
| WO | WO 2008134107 | 11/2008 |
| WO | WO 2008134185 | 11/2008 |

(56) References Cited

FOREIGN PATENT DOCUMENTS

| | | |
|---|---|---|
| WO | WO 2008134545 | 11/2008 |
| WO | WO 2008150633 | 12/2008 |
| WO | WO 2008152588 | 12/2008 |
| WO | WO 2008154312 | 12/2008 |
| WO | WO 2008154504 | 12/2008 |
| WO | WO 2009001108 | 12/2008 |
| WO | WO 2009003989 | 1/2009 |
| WO | WO 2009006615 | 1/2009 |
| WO | WO 2009008001 | 1/2009 |
| WO | WO 2009013501 | 1/2009 |
| WO | WO 2009013670 | 1/2009 |
| WO | WO 2009023247 | 2/2009 |
| WO | WO 2009029453 | 3/2009 |
| WO | WO 2009035759 | 3/2009 |
| WO | WO 2009036334 | 3/2009 |
| WO | WO 2009042379 | 4/2009 |
| WO | WO 2009049252 | 4/2009 |
| WO | WO 2009051829 | 4/2009 |
| WO | WO 2009051830 | 4/2009 |
| WO | WO 2009063377 | 5/2009 |
| WO | WO 2009063421 | 5/2009 |
| WO | WO 2009072079 | 6/2009 |
| WO | WO 2009076363 | 6/2009 |
| WO | WO 2009079589 | 6/2009 |
| WO | WO 2009081262 | 7/2009 |
| WO | WO 2009081348 | 7/2009 |
| WO | WO 2009091851 | 7/2009 |
| WO | WO 2009098648 | 8/2009 |
| WO | WO 2009105337 | 8/2009 |
| WO | WO 2009111664 | 9/2009 |
| WO | WO 2009126653 | 10/2009 |
| WO | WO 2009137661 | 11/2009 |
| WO | WO 2009140251 | 11/2009 |
| WO | WO 2009145801 | 12/2009 |
| WO | WO 2009146082 | 12/2009 |
| WO | WO 2009155335 | 12/2009 |
| WO | WO 2010000085 | 1/2010 |
| WO | WO 2010007573 | 1/2010 |
| WO | WO 2010007574 | 1/2010 |
| WO | WO 2010008424 | 1/2010 |
| WO | WO 2010009100 | 1/2010 |
| WO | WO 2010010473 | 1/2010 |
| WO | WO 2010011833 | 1/2010 |
| WO | WO 2010019778 | 2/2010 |
| WO | WO 2010021589 | 2/2010 |
| WO | WO 2010023591 | 3/2010 |
| WO | WO 2010025428 | 3/2010 |
| WO | WO 2010025431 | 3/2010 |
| WO | WO 2010029054 | 3/2010 |
| WO | WO 2010037828 | 4/2010 |
| WO | WO 2010042034 | 4/2010 |
| WO | WO 2010043054 | 4/2010 |
| WO | WO 2010045460 | 4/2010 |
| WO | WO 2010051551 | 5/2010 |
| WO | WO 2010052275 | 5/2010 |
| WO | WO 2010057049 | 5/2010 |
| WO | WO 2010062675 | 6/2010 |
| WO | WO2010075115 | 7/2010 |
| WO | WO2010080843 | 7/2010 |
| WO | WO 2010107563 | 9/2010 |
| WO | WO2010115194 | 10/2010 |
| WO | WO 2010135516 | 11/2010 |
| WO | WO2012104657 | 8/2012 |
| WO | WO2012158190 | 11/2012 |
| WO | WO2013012869 | 1/2013 |

OTHER PUBLICATIONS

Baskiyar, S. "A Real-time Fault Tolerant Intra-body Network" Dept. Of Comp. Sci & Soft Eng; Auburn University; Proceedings of the 27th Annual IEEE Conference; 0742-1303/02 (2002) IEEE; 6 pp.
Evanczuk, S., "PIC MCU software library uses human body for secure communications link" EDN Network; edn.com; Feb. 26, 2013 Retrieved from internet Jun. 19, 2013 at http://www.edn.com/electronics-products/other/4407842/PIC-MCU-software-library-uses-human-body-for-secure-communications-link; 5 pp.
AADE, "AADE 37th Annual Meeting San Antonio Aug. 4-7 2010" American Association of Diabetes Educators (2010); http://www.diabeteseducator.org/annualmeeting/2010/index.html; 2 pp.
Arshak et al., A Review and Adaptation of Methods of Object Tracking to Telemetry Capsules IC-Med (2007) vol. 1, No. 1, Issue 1, 12 pp.
"ASGE Technology Status Evaluation Report: wireless capsule endoscopy" American Soc. For Gastrointestinal Endoscopy (2006) vol. 63, No. 4; 7 pp.
Aydin et al., "Design and implementation considerations for an advanced wireless interface in miniaturized integrated sensor Microsystems" Sch. of Eng. & Electron., Edinburgh Univ., UK; (2003); abstract.
Barrie, Heidelberg pH capsule gastric analysis. Texbook of Natural Medicine, (1992), Pizzorno, Murray & Barrie.
Brock, "Smart Medicine: The Application of Auto-ID Technology to Healthcare" Auto-ID Labs (2002) http://www.autoidlabs.org/uploads/media/MIT-AUTOID-WH-010.pdf.
Carlson et al., "Evaluation of a non-invasive respiratory monitoring system for sleeping subjects" Physiological Measurement (1999) 20(1): 53.
Delvaux et al., "Capsule endoscopy: Technique and indications" Clinical Gastoenterology (2008) vol. 22, Issue 5, pp. 813-837.
Fawaz et al., "Enhanced Telemetry System using CP-QPSK Band—Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng. (2007) 54(12: 2231-6; abstract.
Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.
Halthion Medical Technologies "Providing Ambulatory Medical Devices Which Monitor, Measure and Record" webpage. Online website: http://www.halthion.com/; downloaded May 30, 2012.
Heydari et al., "Analysis of the PLL jitter due to power/ground and substrate noise"; IEEE Transactions on Circuits and Systems (2004) 51(12): 2404-16.
Hoover et al., "Rx for health: Engineers design pill that signals it has been swallowed" University of Florida News (2010) 2pp.; http://news.ufl.edu/2010/03/31/antenna-pill-2/.
Hotz "The Really Smart Phone" The Wall Street Journal, What They Know (2011); 6 pp.; http://online.wsj.com/article/SB10001424052748704547604576263261679848814.html?mod=djemTECH_t.
ISFET—Ion Sensitive Field-Effect Transistor; Microsens S.A. pdf document. Office Action dated Jun. 13, 2011 for U.S. Appl. No. 12/238,345; 4pp.
Intromedic, MicroCam Innovative Capsule Endoscope Pamphlet. (2006) 8 pp (http://www.intromedic.com/en/product/productinfo.asp).
Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" (2010); http://www.artificialpancreasproject.com/; 3 pp.
Li, P-Y, et al. "An electrochemical intraocular drug delivery device", Sensors and Actuators A 143 (2008) p. 41-48.
Lifescan, "OneTouch UltraLink™" http://www.lifescan.com/products/meters/ultralink (2010) 2 pp.

(56) References Cited

OTHER PUBLICATIONS

MacKay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.

MacKay et al., "Endoradiosonde" Nature, (1957) 1239-1240, 179 Nature Publishing Group.

McKenzie et al., "Validation of a new telemetric core temperature monitor" J. Therm. Biol. (2004) 29(7-8):605-11.

Medtronic, "CareLink Therapy Management Software for Diabetes" (2010); https://carelink.minimed.com/patient/entry.jsp?bhcp=1; 1 pp.

Medtronic, "Carelink™ USB" (2008) http://www.medtronicdiabetes.com/pdf/carelink_usb_factsheet.pdf 2pp.

Medtronic "The New MiniMed Paradigm® REAL-Time Revel™ System" (2010) http://www.medtronicdiabetes.com/products/index.html; 2 pp.

Medtronic, "MINI MED Paradigm® Revel ™ Insulin Pump" (2010) http://www.medtronicdiabetes.com/products/insulinpumps/index.html; 2 pp.

Medtronic, Mini Med Paradigm™ Veo™ System: Factsheet (2010). http://www.medtronic-diabetes.com.au/downloads/Paradigm%20Veo%20Factsheet.pdf ; 4 pp.

Melanson, "Walkers swallow RFID pills for science" Engadget (2008); http://www.engadget.com/2008/07/29/walkers-swallow-rfid-pills-for-science/.

Minimitter Co. Inc. "Actiheart" Traditional 510(k) Summary. Sep. 27, 2005.

Minimitter Co. Inc. Noninvasive technology to help your studies succeed. Mini Mitter.com Mar. 31, 2009.

Mini Mitter Co, Inc. 510(k) Premarket Notification Mini-Logger for Diagnostic Spirometer. 9-21 (1999).

Mini Mitter Co, Inc. 510(k) Premarket Notification for VitalSense. Apr. 22, 2004.

Minimitter Co. Inc. VitalSense Integrated Physiological Monitoring System. Product Description. (2005).

Minimitter Co. Inc. VitalSense Wireless Vital Signs Monitoring Temperatures.com Mar. 31, 2009.

Mojaverian et al., "Estimation of gastric residence time of the Heidelberg capsule in humans: effect of varying food composition" Gastroenterology (1985) 89:(2): 392-7.

"New 'smart pill' to track adherence" E-Health-Insider (2010) http://www.e-healthinsider.com/news/5910/new_'smart_pill'_monitors_medicines.

NPL_AntennaBasics.pdf, Radio Antennae, http://www.erikdeman.de/html/sail018h.htm; (2008) 3pp.

Owano, N., "Study proposes smart sutures with sensors for wounds" Phys.Org. Aug. 2012. http://phys.org/news/2012-08-smart-sutures-sensors-wounds.html.

Park, "Medtronic to Buy MiniMed for $3.7 Billion" (2001) HomeCare; http://homecaremag.com/mag/medical_medtronic_buy_minimed/; 2 pp.

Philips Respironics (http/minimitter.com/products.cfm) Products, Noninvasive Technology to Help Your Studies Succeed. 510(k) Permanent Notification for Vital Sense. Apr. 22, 2004.

"RFID "pill" monitors marchers" RFID News (2008) http://www.rfidnews.org/2008/07/23/rfid-pill-monitors-marchers/.

Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.

Santini, J.T. et al, "Microchips as controlled drug delivery-devices", Agnew. Chem. Int. Ed. (2000), vol. 39, p. 2396-2407.

"SensiVida minimally invasive clinical systems" Investor Presentation Oct. 2009 28pp; http://www.sensividamedtech.com/SensiVidaGeneralOctober09.pdf.

Shawgo, R.S. et al. "BioMEMS from drug delivery", Current Opinion in Solid State and Material Science 6 (2002), p. 329-334.

Shrivas et al., "A New Platform for Bioelectronics-Electronic Pill", Cummins College, (2010).; http://www.cumminscollege.org/downloads/electronics_and_telecommunication/New sletters/Current%20Newsletters.pdf; First cited in third party client search conducted by Patent Eagle Search May 18, 2010 (2010).

"Smartlife awarded patent for knitted transducer" Innovation in Textiles News: http://www.innovationintextiles.com/articles/208.php; 2pp. (2009).

"The SmartPill Wireless Motility Capsule" Smartpill, The Measure of GI Health; (2010) http://www.smartpillcorp.com/index.cfm?pagepath=Products/The_SmartPill_Capsule &id=17814.

Solanas et al., "RFID Technology for the Health Care Sector" Recent Patents on Electrical Engineering (2008) 1, 22-31.

Soper, S.A. et al. "Bio-Mems Technologies and Applications", Chapter 12, "MEMS for Drug Delivery", p. 325-346 (2007).

Swedberg, "University Team Sees Ingestible RFID Tag as a Boon to Clinical Trials" RFID Journal Apr. 27, 2010; http://www.rfidjournal.com/article/view/7560/1.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.

Tatbul et al., "Confidence-based data management for personal area sensor networks" ACM International Conference Proceeding Series (2004) 72.

Tierney, M.J. et al "Electroreleasing Composite Membranes for Delivery of Insulin and other Biomacromolecules", J. Electrochem. Soc., vol. 137, No. 6, Jun. (1990), p. 2005-2006.

Walkey, "MOSFET Structure and Processing"; 97.398* Physical Electronics Lecture 20; Office Action dated Jun. 13, 2011 for U.S. Appl. No. 12/238,345; 24 pp.

Xiaoming et al., "A telemedicine system for wireless home healthcare based on bluetooth and the internet" Telemedicine Journal and e-health (2004) 10(S2): S110-6.

Yang et al., "Fast-switching frequency synthesizer with a discriminator-aided phase detector" IEEE Journal of Solid-State Circuits (2000) 35(10): 1445-52.

Yao et al., "Low Power Digital Communication in Implantable Devices Using Volume Conduction of Biological Tissues" Proceedings of the 28th IEEE, EMBS Annual International Conference, Aug. 30-Sep. 3, 2006.

Zimmerman, "Personal Area Networks: Near-field intrabody communication" IBM Systems Journal (1996) 35 (3-4):609-17.

Description of ePatch Technology Platform for ECG and EMG, located it http://www.madebydelta.com/imported/images/DELTA_Web/documents/Me/ePatch_ECG_EMG.pdf, Dated Sep. 2, 2010.

Zworkin, "A Radio Pill" Nature, (1957) 898, 179 Nature Publishing Group.

Nikander et al., "The Adaptive Delivery System in a Telehealth Setting: Patient Acceptance, Performance and Feasibility" Journal of Aerosol Medicine and Pulmonary Drug Delivery; vol. 23, Supp. 1, (2010) pp. S21-S27.

Lifescan, "OneTouch UltraLink™" http://www.lifescan.com/products/meters/ultralink, (Jul. 2010), 2 pp.

Medtronic, "Carelink™ USB"(Dec. 2011) http://www.medtronicdiabetes.com/pdf/carelink_usb_factsheet.pdf 2pp.

Medtronic "The New MiniMed Paradigm® Real-Time Revel™ System" http://www.medtronicdiabetes.com/products/index.html; 2 pp, (Aug . 2010).

Medtronic, "MINI MED Paradigm® Revel ™ Insulin Pump"(Jul . 2010), http://www.medtronicdiabetes.com/products/insulinpumps/index.html; 2 pp.

* cited by examiner

Prior Art

DATA GATHERING SYSTEM

CROSS-REFERENCE TO RELATED APPLICATIONS

This application claims priority pursuant to the 35 U.S.C. §119 to U.S. application Ser. No. 61/300,435 filed Feb. 1, 2010, and entitled "Two-wrist data-gathering system" and to U.S. application Ser. No. 61/378,878 filed Aug. 31, 2010, and entitled "Data Gathering System". Each of the foregoing is incorporated by reference in its entirety.

INTRODUCTION

Some electromagnetic communications, e.g., EKG signals, conductance communications, RF signals, etc., are very, very difficult to detect and gather, except with inconvenient or awkward data-gathering systems. The general ambient conditions can contribute noise in whichever portion of the EM spectrum is being investigated. The source of the desired EM signal (for example a device within a live subject) may be overwhelmed or nearly overwhelmed by naturally occurring signals in the subject. The data-gathering device will likely contain a microcontroller and other electronics that will emit signals that further degrade the signal-to-noise ratio for the data gathering.

Perhaps more subtly, but also very importantly, parasitic capacitances, however small in absolute terms, can suck away electromagnetic energy at the frequency band of interest. Sources of parasitic capacitance can include relative positions of pairs of sensing electrodes, relative position of any single electrode relative to circuit boards containing ground planes, and the relative position of any single electrode relative to large metallic or conductive bodies such as batteries or power cells.

One example of a device within a live subject that may transmit a signal of interest is the ingestible event marker ("IEM") described in US patent publication 2010-0185055 entitled "Ingestible event marker systems", US patent publication 20100081894 entitled "Communication system with partial power source", US patent publication 20100022836 entitled "In-body device having a multi-directional transmitter", US patent publication 20090256702 entitled "multimode communication ingestible event markers and systems, and methods of using same", US patent publication number 20090135886 entitled "Transbody communication systems employing communications channels", and US patent publication number 20090082645 entitled "In-body device with virtual dipole signal amplification", US patent publication number 20100312188 entitled "Body-Associated Receiver and Method", each of which is incorporated herein by reference.

Such an IEM is necessarily extremely limited in the amount of electrical power available, and in the size of antenna available to couple the transmitter to nearby transmission media. The emitted signal is thus not much stronger than typical ambient noise sources. Heretofore the detection of such IEM signals has required the use of a patch, the patch having a form factor not unlike a large adhesive bandage, the patch applied to the abdomen of a subject so as to be nearby to the IEM when it emits its signal. The patch has potential drawbacks, among them the risk of irritation to the epidermis due to the adhesive attachment, possible interference with freedom of movement, and perhaps aesthetically displeasing appearance to some eyes.

Figure 2:
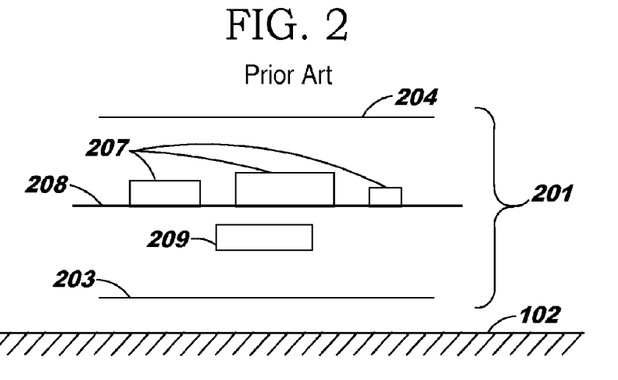
FIG. 2 shows a possible sensing device according to the prior art in cross-sectional view.

An example of a data-gathering system that might be attempted is shown in FIG. 2. In such a system 201, the goal is to pick up a signal detectable as between (a) a surface 102 such as tissue of a subject, and (b) the "air" or general ambient region (located everywhere else in FIG. 2 besides the tissue and the detecting system). The pickup of signals is accomplished by electrode 203, which is coupled to the surface 102, and electrode 204, which is coupled to the "air". Circuit board 208 carries circuitry 207 and is connected with battery or cell ("battery") 209. The circuitry 207 is connected to the electrodes 203, 204. The hope is that a differential amplifier in the electronics 207 could take as its input each of the two electrodes 203, 204 and thereby detect signals of interest. The system 201 might be dry-coupled to tissue (as distinguished from the adhesive patch just described) and might be conveniently located elsewhere than the abdomen, for example in a bracelet or wristband, if only under such circumstances it proved to be possible to successfully detect the signals of interest.

Experience shows, however, that at frequencies of interest (perhaps tens of kilohertz), the parasitic capacitances present in such a device 201 cause a loss of a large portion of any detected signal. The parasitic capacitances may be conveniently modeled as being present between electrode 204 and the ground plane of circuit board 208, between electrode 204 and battery 209, between electrode 203 and the ground plane of circuit board 208, and between electrode 203 and battery 209. Some parasitic capacitance likely develops as well between the electrode 203 and the electrode 204.

Experience also shows that RFI (radio frequency interference) is likely to be emitted by the electronics 207 and then picked up by the electrodes 203, 204. The desirably small form factor of a device 201 will obviate the use of traditional ferrite chokes and the like that might otherwise be used to try to choke off some of the coupling paths for RFI. The small form factor also juxtaposes the electrodes and the RFI sources with very little physical separation.

One approach sometimes employed to attempt to reduce RFI is to "can" the source of the RFI. In a device 201 this might be done by putting a metal shroud of a suitably selected metal or alloy around the circuitry 207. While this approach may indeed reduce RFI, it has the drawback of introducing still greater parasitic capacitances as between electrodes 203, 204.

It would be very desirable if a way could be found to detect such faint electrical signals reliably, in ways that would be more consistently acceptable to the subject than prior-art approaches. If a way could be found, it might be less irritating to the epidermis, might interfere less or not at all with freedom of movement, and might be more aesthetically pleasing to some eyes.

SUMMARY

A device for gathering data has first and second electrodes. The first electrode is coupled to a surface of interest, and the second electrode is coupled to "everything else" or "the air". The first electrode is shielded from the second, and from most sources of parasitic capacitance, by a shield that is driven by an active driver that drives the shield to track, and ideally to match, the instantaneous potential of the electrode. The second electrode is likewise shielded in a similar way from most sources of parasitic capacitance. These shields likewise help to limit the extent to which RFI from the device electronics couples with either of the electrodes. In this way the sensing device achieves a markedly better signal-to-noise ratio at frequency bands of interest.

DETAILED DESCRIPTION

Figure 1:
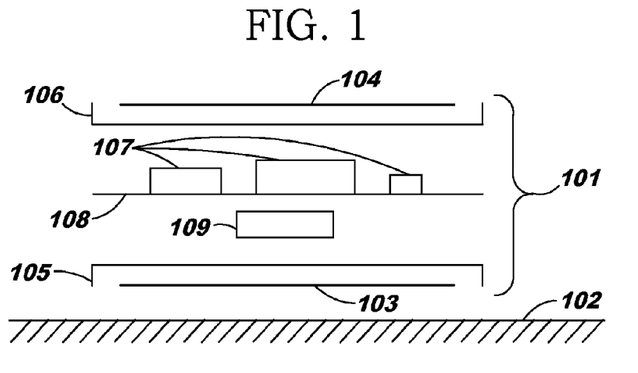
FIG. 1 shows a sensing device according to the invention in cross-sectional view.

Turning to FIG. 1, what is shown is a sensing device 101 according to the invention in cross-sectional view. The sensing device has first and second electrodes 103 and 104. The first electrode 103 is coupled to a surface of interest 102, which might be tissue of a living subject, and the second electrode 104 is coupled to "everything else" or "the air". Although it is largely a matter of semantics, one might choose to characterize the second electrode 104 as an electrode coupling to "ground" or "space ground".

The first electrode 103 is shielded from the second electrode 104, and from most sources of parasitic capacitance, by a shield 105 that is driven by an active driver (omitted for clarity in FIG. 1) that drives the shield 105 to track, and ideally to match, the instantaneous potential of the electrode 103. The second electrode 104 is likewise shielded in a similar way from most sources of parasitic capacitance by a shield 106. These shields 105, 106 likewise help to limit the extent to which RFI from the device electronics 107 couples with either of the electrodes 103, 104. In this way the sensing device 101 achieves a markedly better signal-to-noise ratio at frequency bands of interest as compared with prior-art sensing devices.

Were it not for the shielding effects of shields 105, 106, the electrodes 103, 104 would capacitively couple parasitically with the battery 109, with ground planes in the circuit board 108, and with each other.

Figure 3:
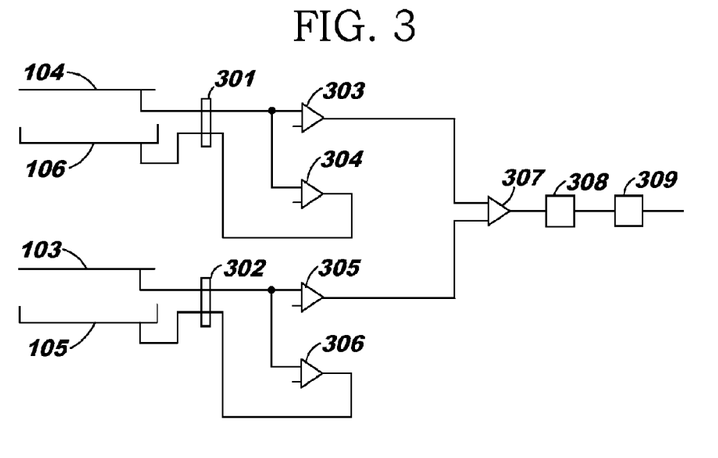
FIG. 3 shows the sensing device of FIG. 1 in functional block diagram portrayal.

FIG. 3 shows the sensing device 101 of FIG. 1 in functional block diagram portrayal. Electrode/shield assembly 104/106 plugs via connector 301 to the circuit board 108. Electrode/shield assembly 103/105 likewise plugs via connector 302 to the circuit board 108. The signal detected at electrode 104 is amplified in amplifier 304, which drives shield 106. The signal detected at electrode 103 is amplified in amplifier 306, which drives shield 105. The signal detected at electrode 104 is also amplified in amplifier 303, providing one of two inputs to differential amplifier 307. The signal detected at electrode 103 is also amplified in amplifier 305, providing the other of two inputs to differential amplifier 307. The resulting signal (a difference between the instantaneous potentials at the two electrodes) can then be filtered by a bandpass filter 308 and converted to a digital signal by analog-to-digital converter 309.

It will be appreciated that the amplifier 304 will need to be selected to have a frequency response sufficient to drive shield 106 at the frequency band of interest and preferably at some higher frequencies. The amplifier 304 will also need to be selected to have enough power to pump sufficient charge into and out of the shield 106 taking into account its physical size and impedance. The same may be said of amplifier 306 relative to its respective shield 105.

In an exemplary aspect the frequency band of interest is 54 kilohertz plus or minus five kilohertz. Thus bandpass filter 308 is chosen to pass this band. It is thought, however, that some IEMs could be developed that emit signals at a megahertz or higher, in which case the data collection device 101 would desirably carry out its function at such frequency bands. Other devices 101 could use a frequency band at about 20 kilohertz.

It will be appreciated that amplifiers 303, 305, and 307, and filter 308, and A/D converter 309 each need to have frequency response sufficient for the frequency band of interest. It will be further appreciated that although the circuitry of FIG. 3 is depicted with discrete components such as individual op amps 303, 304, 305, 306, 307 and discrete-component active filter 308, the benefits of the invention could just as well be gained by substituting a digital signal processor of sufficient frequency response for some or most of the components portrayed in FIG. 3, without departing in any way from the invention. The amplifiers 304, 306 need to have high gain at the frequencies of interest and need to have low noise.

In the present proof-of-concept aspect, a microcontroller (omitted for clarity in FIG. 3) receives signals which are stored as data in the microcontroller (or in memory attached to the microcontroller), and the data can then be communicated external to the device 101, for example to a general-purpose computer executing appropriate software for analysis of the received signals. The circuitry 107 is powered by a small "button" cell or battery. Another approach would be to communicate the data wirelessly, for example via Bluetooth, to equipment external to the device 101. Such equipment may be a smart mobile phone running a suitable application to receive data via Bluetooth and to transmit the data further to a remote host, via GPRS or other mobile-phone data protocol.

In the present proof-of-concept aspect, the device 101 is a flat square device, 3 centimeters square. It is able to provide a wearable wristwatch form factor, only slightly larger than the button cell being used to power the device 101.

The desirable result is to pick up the signals of interest from a single distal point such as a wrist. The coupling would be by means of a non-sticky dry electrode with capacitive coupling to the body, or in some cases with electrically conductive coupling to the body. From a user's point of view this might be an elastic belt around the waist or chest, or an elastic wristlet band, or a necklace form factor.

The electrode 103 may be gold, or platinum, or stainless steel.

The active shielding accomplished with shields 105, 106 driven by drivers 304, 306 permits the device 101 to pick up signals such as IEM signals despite being further away from the IEM than the prior-art adhesive-bandage type of patch, and despite being non-sticky. This makes the system of device and IEM more acceptable to users.

Further shielding may be disposed around the circuitry 107, connected for example to a ground plane within the circuit board 108, or connected for example to a potential defined to be between the rails defined by the battery.

It will be appreciated that devices 101 could be used in pairs, each touching a body at a different place. The two devices 101 are each coupled with "space ground" and are thus to some extent coupled to each other, through the electrodes 104. The paired devices could then collect data from the body in a somewhat "dipole" receiver arrangement.

Those skilled in the art will have no difficulty devising myriad obvious variants and improvements of the aspects set forth here, without departing in any way from the invention, all of which obvious variants and improvements are intended to be encompassed by the claims which follow.

The invention claimed is:

1. Apparatus for gathering data, the apparatus comprising:
   a first electrode, the first electrode characterized as non-sticky, the first electrode disposed for capacitive or electrically conductive coupling with a surface having air thereabove;
   a second electrode, the second electrode characterized as non-sticky, the second electrode disposed for capacitive or electrically conductive coupling with the air;

electronic circuitry disposed physically between the first and second electrodes;

the first electrode shielded by a first shield physically located between the first electrode and the electronic circuitry;

the second electrode shielded by a second shield located physically between the second electrode and the electronic circuitry;

the electronic circuitry comprising a first driver receiving as an input a signal present at the first electrode, the first driver having an output coupled with the first shield;

the electronic circuitry comprising a second driver receiving as an input a signal present at the second electrode, the second driver having an output coupled with the second shield;

the electronic circuitry further comprising a differential amplifier having first and second inputs, each input connected to a respective one of the first and second electrodes;

the differential amplifier having an output;

the electronic circuitry further comprising means communicating data indicative of the output of the differential amplifier to equipment external to the apparatus; and a third shield surrounding the electronic circuitry, the third shield disposed physically between the first shield and the second shield, the third shield electrically insulated from the first shield, and the third shield electrically insulated from the second shield.

2. The apparatus of claim 1 wherein the means communicating data indicative of the output of the differential amplifier to equipment external to the apparatus comprises a connector providing a serial data path.

3. The apparatus of claim 1 wherein the means communicating data indicative of the output of the differential amplifier to equipment external to the apparatus comprises a Bluetooth link.

4. The apparatus of claim 1 wherein the output of the differential amplifier is bandpass filtered to a band including 54 kilohertz.

5. The apparatus of claim 1 further characterized as unpowered from outside of the apparatus.

6. The apparatus of claim 1 further characterized in that the coupling of the second electrode with the air is free of any intervening conducting or insulating material.

7. The apparatus of claim 6 further characterized in that nothing lies between the second electrode and the air.

8. A method for use in detecting signals, the method comprising the steps of:

providing an apparatus comprising:

a first electrode, the first electrode characterized as non-sticky, the first electrode capacitively or electrically conductively coupled with a surface having air thereabove;

a second electrode, the second electrode characterized as non-sticky, the second electrode capacitively coupled with the air;

electronic circuitry physically between the first electrode and the second electrode;

a first shield physically between the first electrode and the electronic circuitry;

a second shield physically between the second electrode and the electronic circuitry; and a third shield surrounding the electronic circuitry, the third shield disposed physically between the first shield and the second shield, the third shield 3electrically insulated from the first shield, and the third shield electrically insulated from the second shield by means of the electronic circuitry, driving the first shield to follow a signal present at the first electrode;

by means of the electronic circuitry, driving the second shield to follow a signal present at the second electrode;

by means of the electronic circuitry, deriving a difference between the signal present at the first electrode and the signal present at the second electrode; and communicating data indicative of the difference to equipment external to the apparatus.

9. The method of claim 8 wherein communicating data indicative of the difference to equipment external to the apparatus comprises passing serial data through a connector providing a serial data path.

10. The method of claim 8 wherein communicating data indicative of the difference to equipment external to the apparatus comprises passing data through a Bluetooth link.

11. The method of claim 8 wherein the surface is skin.

12. The method of claim 11 wherein the skin is at a wrist.

13. The method of claim 8 further comprising filtering the derived difference to a band including 54 kilohertz, the communicating step further characterized in that the communicated data is indicative of the filtered derived difference.

14. The method of claim 8 further characterized in that the coupling of the second electrode with the air is free of any intervening conducting or insulating material.

15. The method of claim 14 further characterized in that nothing lies between the second electrode and the air.

* * * * *